(12) United States Patent
Rekken et al.

(10) Patent No.: US 10,030,037 B2
(45) Date of Patent: Jul. 24, 2018

(54) DIAMINOSILANE COMPOUNDS

(71) Applicant: Dow Corning Corporation, Midland, MI (US)

(72) Inventors: Brian D. Rekken, Midland, MI (US); Xiaobing Zhou, Midland, MI (US)

(73) Assignee: DOW SILICONES CORPORATION, Midland, MI (US)

( * ) Notice: Subject to any disclaimer, the term of this patent is extended or adjusted under 35 U.S.C. 154(b) by 0 days.

(21) Appl. No.: 15/314,300

(22) PCT Filed: May 29, 2015

(86) PCT No.: PCT/US2015/033075
§ 371 (c)(1),
(2) Date: Nov. 28, 2016

(87) PCT Pub. No.: WO2015/184202
PCT Pub. Date: Dec. 3, 2015

(65) Prior Publication Data
US 2017/0129908 A1    May 11, 2017

Related U.S. Application Data

(60) Provisional application No. 62/004,922, filed on May 30, 2014.

(51) Int. Cl.
| | |
|---|---|
| C07F 7/18 | (2006.01) |
| C07F 7/10 | (2006.01) |
| C07F 7/12 | (2006.01) |
| H01L 21/02 | (2006.01) |
| C23C 16/455 | (2006.01) |
| C23C 16/24 | (2006.01) |
| C23C 16/34 | (2006.01) |
| C23C 16/40 | (2006.01) |

(52) U.S. Cl.
CPC .............. *C07F 7/10* (2013.01); *C07F 7/12* (2013.01); *C07F 7/126* (2013.01); *C23C 16/24* (2013.01); *C23C 16/345* (2013.01); *C23C 16/401* (2013.01); *C23C 16/45553* (2013.01); *H01L 21/0217* (2013.01); *H01L 21/0262* (2013.01); *H01L 21/02164* (2013.01); *H01L 21/02219* (2013.01); *H01L 21/02271* (2013.01); *H01L 21/02532* (2013.01)

(58) Field of Classification Search
None
See application file for complete search history.

(56) References Cited

U.S. PATENT DOCUMENTS

| | | | |
|---|---|---|---|
| 4,546,008 A | 10/1985 | Saitoh et al. | |
| 7,875,312 B2 | 1/2011 | Thridandam et al. | |
| 7,875,556 B2 | 1/2011 | Xiao et al. | |
| 8,445,367 B2 | 5/2013 | Noh et al. | |
| 8,658,284 B2 | 2/2014 | Chen et al. | |
| 8,686,173 B2 | 4/2014 | Knies et al. | |
| 8,753,984 B2 | 6/2014 | Murakami et al. | |
| 8,993,072 B2 | 3/2015 | Xiao et al. | |
| 9,758,865 B2 | 9/2017 | Hasebe et al. | |
| 2008/0207007 A1 | 8/2008 | Thridandam et al. | |
| 2009/0291872 A1 | 11/2009 | Bara et al. | |
| 2013/0109155 A1 | 5/2013 | Okada et al. | |
| 2013/0319290 A1 | 12/2013 | Xiao et al. | |
| 2013/0323435 A1 | 12/2013 | Xiao et al. | |
| 2015/0024608 A1 | 1/2015 | Mayorga et al. | |
| 2015/0037970 A1 | 2/2015 | Hasebe et al. | |
| 2015/0094470 A1 | 4/2015 | Sanchez et al. | |

OTHER PUBLICATIONS

Tamao et al., Organometallics 1997, 16, 780-788.*
Stueger et al., Monatshefte fuer Chemie (1994), 125(6-7), 615-22.; see also STN abstract.*
Stuger et al., Monatshefte Fuer Chemie (1994), 125(6-7), 615-22. (Year: 1994).*
David R. Kanis et al: "Nonlinear Optical Characteristics of Novel Inorganic Chromophores Using the Zindo Formalism", Journal of Materials Chemistry A: Materials for Energy and Sustainability, vol. 3, No. 1, Jan. 1, 1991 (Jan. 1, 1991), pp. 19-22.
Waltraud Gollner et al: "Linear and Cyclic Polysilanes Containing the Bis(tnmethylsilyl)aniino Group: Synthesis, Reactions, and Spectroscopic Characterization", Inorganic Chemistry, vol. 42, No. 15, Jul. 1, 2003 (Jul. 1, 2003), pp. 4579-4584.
Heinz Schuh et al: "Disilanyl-amines—Compounds Comprising the Structure Unit Si—Si—N, as Single-Source Precursors for Plasma-Enhanced Chemical Vapor Deposition (PE-CVD) of Silicon Nitride", Zeitschrift Fur Anorganische Uno Allgemeine Chemie, Wiley—V C H Verlag GMBH & Co. KGAA, DE, vol. 619, Aug. 1, 1993 (Aug. 1, 1993), pp. 1347-1352.
Blum, Y.; Laine, R. M., Catalytic methods for the synthesis of oligosilazanes, Organometallics (1986), 5(10), 2081-6.
David J. Liptrot, Professor Michael S. Hill,* and Mary F. Mahon, Accessing the Single-Electron Manifold: Magnesium-mediated Hydrogen Release from Silanes, Angew. Chem. Int. Ed. 2014, 53, 6224-6227.
Dunne, James F.; Neal, Steven R.; Engelkemier, Joshua; Ellern, Arkady; Sadow, Aaron D., Tris(oxazolinyl) boratomagnesium-Catalyzed Cross-Dehydrocoupling of Organosilanes with Amines, Hydrazine, and Ammonia, Journal of the American Chemical Society (2011), 133(42), 16782-16785.
Dunne, James F.; Sadow, Aaron D., Magnesium catalyzed N—Si bond formation: Dehydrocoupling of silanes and amines, Abstracts of Papers, 239th ACS National Meeting, San Francisco, CA, United States, Mar. 21-25, 2010 (2010), INOR-1139.
Greb, Lutz; Tamke, Sergej; Paradies, Jan, Catalytic metal-free Si—N cross-dehydrocoupling, Chemical Communications (Cambridge, United Kingdom) (2014), 50(18), 2318-2320.
H. Stuger et al., Aminoderviate hydrierter Oligosilane: Darstellung, Charakterisierung und Eigenschaften, Monatshefte für Chemie Chemical Monthlo, vol. 125, pp. 615-622, 1994.

(Continued)

*Primary Examiner* — Clinton A Brooks
*Assistant Examiner* — Kofi Adzamli
(74) *Attorney, Agent, or Firm* — Matthew T. Fewkes

(57) ABSTRACT

Disclosed is a compound of formula (I): $(R^1 R^2N)Si_nH_{2n}(NR^3R^4)$ (I) wherein subscript n, $R^1$, $R^2$, $R^3$ and $R^4$ are as defined herein. Also disclosed are a method of making, intermediates useful therein, method of using, and composition comprising the compound of formula (I).

7 Claims, No Drawings

(56) References Cited

OTHER PUBLICATIONS

He, Jiliang; Liu, Hua Qin; Harrod, John F.; Hynes, Rosie, Dehydrocoupling reactions of organosilanes with hydrazines, Organometallics (1994), 13(1), 336-43.

Hill, Michael S.; Liptrot, David J.; MacDougall, Dugald J.; Mahon, Mary F.; Robinson, Thomas P., Hetero-dehydrocoupling of silanes and amines by heavier alkaline earth catalysis, Chemical Science (2013), 4(11), 4212-4222.

Huhert Schmidbaur et al.. Difference in React ivi ty of I,4-Disi labutane and n -Tetrasilane tow8rds Secondary Amines. Zeitschrift fur Naturforschung B. vol. 45. Issue 12. pp. 1679-1683, Dec. 1990 See p. 1680. compounds 9 and 10.

Itagaki, Shintaro; Kamata, Keigo; Yamaguchi, Kazuya; Mizuno, Noritaka, Rhodium acetate/base-catalyzed N-silylation of indole derivatives with hydrosilanes, Chemical Communications (Cambridge, United Kingdom) (2012), 48(74), 9269-9271.

Koenigs, C. David F.; Mueller, Maria R; Aiguabella, Nuria; Klare, Hendrik F. T.; Oestreich, Martin, Catalytic dehydrogenative Si—N coupling of pyrroles, indoles, carbazoles as well as anilines with hydrosilanes without added base, Chemical Communications (Cambridge, United Kingdom) (2013), 49(15), 1506-1508.

Liu, H. Q.; Harrod, J. F. , Copper(I)-catalyzed cross-dehydrocoupling reactions of silanes and amines, Canadian Journal of Chemistry (1992), 70(1), 107-10.

Liu, Hua Qin; Harrod, John F., Dehydrocoupling of ammonia and silanes catalyzed by dimethyltitanocene, Organometallics (1992), 11(2), 822-7.

Matarasso-Tchiroukhine, Elisabeth, AreneCr(CO)2(η2-HSiHPh2) complexes as catalysts for the silicon-hydrogen bond activation. Hydrolysis of the silicon-hydrogen bond and dehydrogenative coupling between diphenylsilane and nucleophiles, Journal of the Chemical Society, Chemical Communications (1990)(9), 681-2.

Reichl, Jennifer A.; Berry, Donald H., Recent progress in transition metal-catalyzed reactions of silicon, germanium, and tin, Advances in Organometallic Chemistry (1998), 43, 197-265. | Language: English, Database: CAPLUS.

Sommer, Leo H.; Citron, Joel D., Group VIII metal-catalyzed reactions of organosilicon hydrides with amines, hydrogen halides, and hydrogen sulfide, Journal of Organic Chemistry (1967), 32(8), 2470-2.

Takato Mitsudome,[a] Teppei Urayama,[a] Zen Maeno,[a] Tomoo Mizugaki,[a] Koichiro Jitsukawa,[a] and Kiyotomi Kaneda; Highly Efficient Dehydrogenative Coupling of Hydrosilanes with Amines or Amides Using Supported Gold Nanoparticles, Chem. Eur. J. 2015, 21, 3202-3205.

Tsuchimoto, Teruhisa; Iketani, Yoshihiko; Sekine, Masaru, Zinc-Catalyzed Dehydrogenative N-Silylation of Indoles with Hydrosilanes, Chemistry—A European Journal (2012), 18(31), 9500-9504, S9500/1-S9500/90.

Wang, Jia Xi; Dash, Aswini K.; Berthet, Jean Claude; Ephritikhine, Michel; Eisen, Mods S., Dehydrocoupling reactions of amines with silanes catalyzed by [(Et2N)3U][BPh4], Journal of Organometallic Chemistry (2000), 610(1-2), 49-57.

Wang, Wei Dong; Eisenberg, Richard, Dehydrogenative coupling reactions to form silazane oligomers promoted by binuclear rhodium complexes, Organometallics (1991), 10(7), 2222-7.

Xie, Weilong; Hu, Hongfan; Cui, Chunming, [(NHC)Yb{N(SiMe3)2}2]-Catalyzed Cross-Dehydrogenative Coupling of Silanes with Amines, Angewandte Chemie, International Edition (2012), 51(44), 11141-11144.

Buch, Frank; Harder, Sjoerd; The Azametallacyclopropane Ca(n2-Ph2CNPh)(hmpa)3: A Calcium Alternative to a Versatile Ytterbium (II) Catalyst, Organometallics 2007, 26, 5132-5135. Universitatsstrasse 5-7.

Tsuchimoto, Teruhisa; Kanbara, Mitsutaka; Reductive Alkylation of Indoles with Alkynes and Hydrosilanes under Indium Catalysis, Organic Letters, 2011, vol. 13, No. 5, 912-915.

Melen, Rebecca; Dehydrocoupling routes to element-element bonds catalysed by main group compounds, Chem. Soc. Rev., 2016, 45, 775-788.

Kinsley, Kermit K., "Catalytic dehydrogenation condensation of silyl hydrides and amines: thermal decomposition of silazanes and polysilazanes " (1988). Retrospective Theses and Dissertations. Paper 8782.

Swihart et al., J. Phys. Chem. B., (1999), v. 103, pp. 64-76.

Wickramanayaka et al., Surtace Science, (1997), v. 18, pp. 108-115.

JP1985-100675 machine translation.

JP1985-026665 machine translation.

\* cited by examiner

DIAMINOSILANE COMPOUNDS

CROSS REFERENCE TO RELATED APPLICATIONS

This application is a U.S. national stage filing under 35 U.S.C. § 371 of PCT Application No. PCT/US15/033075 filed on 29 May 2015, currently pending, which claims the benefit of U.S. Provisional Patent Application No. 62/004922 filed 30 May 2014 under 35 U.S.C. § 119 (e). PCT Application No. PCT/US15/033075 and U.S. Provisional Patent Application No. 62/004922 are hereby incorporated by reference.

The field of this invention generally relates to diaminosilane compounds, compositions comprising same, methods of making and using same, intermediates useful in synthesis of same, and films and silicon materials prepared therefrom.

Elemental silicon, and other silicon materials such as silicon oxide, silicon carbide, silicon nitride, silicon carbonitride, and silicon oxycarbonitride, have a variety of known uses. For example, silicon film may be used as a semiconductor, an insulating layer or a sacrificial layer in the manufacture of electronic circuitry for electronic or photovoltaic devices.

Known methods of preparing the silicon material may use one or more silicon-yielding precursor materials. Use of these precursors is not limited to making silicon for electronic or photovoltaic semiconductor applications. For example, the silicon-yielding precursors may be used to prepare silicon-based lubricants, elastomers, and resins.

Despite decades of research, however, silicon-yielding precursors typically have been small molecules with one or two Si atoms. We believe this is due in part to a perception higher order compounds might be unsuitable as precursors and due to synthetic difficulties accessing higher order compounds, including molecular instability. We see a long-felt need in the electronics and photovoltaic industries for improved silicon-yielding precursors. We think higher order precursors having more than two silicon atoms per molecule would enable lowering of deposition temperatures and making finer semiconductor features for better performing electronic and photovoltaic devices.

BRIEF SUMMARY OF THE INVENTION

We have discovered and synthesized diaminosilane compounds having three to nine silicon atoms and two nitrogen atoms per molecule. Embodiments of the invention include:

A compound of formula (I):

$$(R^1R^2N)Si_nH_{2n}(NR^3R^4) \quad (I)$$

wherein subscript n is an integer from 3 to 9; $R^1$ is methyl, propyl, butyl, pentyl, hexyl, $(C_3-C_6)$cycloalkyl, $(C_2-C_6)$alkenyl, $(C_2-C_6)$alkynyl, or phenyl, and each $R^2$, $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ is H and each of $R^2$, $R^3$, and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^3$ are H and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be —$R^{1a}$—$R^{2a}$— wherein —$R^{1a}$—$R^{2a}$— is $(C_2-C_5)$alkylene and each $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be —$R^{1a}$—$R^{2a}$— wherein —$R^{1a}$—$R^{2a}$— is $(C_2-C_5)$alkylene and $R^3$ and $R^4$ are bonded together to be —$R^{3a}$—$R^{4a}$— wherein —$R^{3a}$—$R^{4a}$— is  $(C_2-C_5)$alkylene; or $R^1$ and $R^3$ are bonded together to be —$R^{1a}$—$R^{3a}$— wherein —$R^{1a}$—$R^{3a}$— is $(C_2-C_5)$alkylene and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; and the $R^1R^2N$— and —$NR^3R^4$ groups are bonded to a same silicon atom or to different silicon atoms in the compound of formula (I).

A composition comprising the compound of formula (I) and at least one additional compound that is different than the compound of formula (I).

A method of making the compound of formula (I), the method comprising: contacting the compound of formula (c1): $(R^1R^2N)Si_nX_{2n}(NR^3R^4)$ (c1), wherein each X independently is a halogen atom selected from Cl, Br, and I; and n, $R^2$, $R^3$ and $R^4$ are as defined above, with an aluminum hydride to give a mixture of the compound of formula (I) and at least one reaction by-product.

A method of making a compound of formula (I), the method comprising:

Contacting a compound of formula (d1): $(R^1R^2N)Si_nH_{2n+1}$ (d1)

with a compound of formula (d2) $HNR^3R^4$ (d2), wherein n, $R^1$, $R^2$, $R^3$, and $R^4$ are as defined above, in the presence of a main group element catalyst, to give a reaction mixture of the compound of formula (I).

A method of making a silicon-containing material, the method comprising subjecting a source gas comprising the compound of formula (I) to silicon deposition conditions in the presence of a substrate, to form a silicon-containing material on the substrate.

The silicon-containing material made by the just above method.

Use of the compound of formula (I) in the making of a silicon-containing material comprising an elemental silicon, a silicon carbide, silicon nitride, silicon oxide, silicon oxynitride, or silicon-carbo-nitride.

The compound of formula (c1).

A method of making the compound of formula (c1), the method comprising: contacting one molar equivalent of a compound of formula (a1): $R^1R^2NM$ (a1) and one molar equivalent of a compound of formula (a2): $R^3R^4NM$ (a2) with a compound of formula (b1): $Si_nX_{2n+2}$ (b1), or contacting one molar equivalent of a compound of formula (a3) $M(R^2)N$—$R^{1a}$—$R^{3a}$—$N(R^4)M$ (a3) with a compound of formula (b1), to give a compound of formula (c1): $(R^1R^2N)Si_nX_{2n}(NR^3R^4)$ (c1), wherein each M independently is a Group I element selected from H, Li, Na, and K; each X independently is a halogen atom selected from Cl, Br, and I; and n, $R^1$, $R^2$, $R^3$, and $R^4$ are as defined immediately above; and the $R^1R^2N$— and —$NR^3R^4$ groups are bonded to a same silicon atom or to different silicon atoms in the compound of formula (c1).

Use of the compound of formula (c1) in the synthesis of the compound of formula (I).

The compounds of formulas (a1), (a2), (a3) and (b1) are useful in making the compound of formula (c1). The compound of formula (c1) is an intermediate useful in making the compound of formula (I). The compound of formula (c1) has additional uses, e.g., as a silicon precursor material, vehicle or solvent, and lubricant. The compound of formula (I) is useful as a silicon-yielding precursor for making a silicon-containing material for electronic and photovoltaic devices. The compounds of formula (I) have additional uses not related to electronic or photovoltaic semiconductor applications, e.g., for making silicon-based lubricants, elastomers, and resins. The invention method may have additional uses unrelated to these applications.

DETAILED DESCRIPTION OF THE INVENTION

The Brief Summary and Abstract are incorporated here by reference. The invention embodiments, uses and advantages summarized above are further described below.

The invention has technical and non-technical advantages. One of the problems solved by the method is providing a new silicon-yielding precursor in the form of the diaminosilane compounds having three to five silicon atoms and two nitrogen atoms per molecule. The solution comprises the compound of formula (I) and provides a synthesis thereof. In some aspects the invention provides a diaminosilane compound of formula (I); alternatively or additionally the invention provides a silicon-yielding precursor compound of formula (I); alternatively or additionally the invention provides a silicon-and-nitrogen-yielding precursor compound of formula (I).

Another advantage it is believed is that the compound of formula (I) may be used as a silicon-yielding precursor to deposit silicon-containing materials using a silicon deposition process temperature that is lower than the temperature used for a comparative compound, $R^1R^2N$—$SiH_2NR^3R^4$ or $R^1R^2N$—$Si_2H_4NR^3R^4$, to prepare a comparable silicon material, if the latter would even be possible This expected benefit would enable a higher deposition rate, a saving of thermal budget (i.e., lower thermal energy), and/or avoiding damage to heat sensitive devices.

Another advantage it is believed is that the compound of formula (I) may be used as a silicon-yielding precursor to deposit silicon-containing materials such as films, making finer semiconductor features for better performing electronic and photovoltaic devices.

It may be convenient to illustrate some further advantages of the invention by using the compounds of formula (I) to form elemental silicon materials such as silicon films with finer microscale features or higher purity than prior art materials.

The invention and advantages are not limited to solutions of the aforementioned problems or to the above advantages. Certain aspects of this invention may independently solve additional problems and/or have other advantages.

Aspects of the invention are described herein using various common conventions. For example, all states of matter are determined at 25° C. and 101.3 kPa unless indicated otherwise. All % are by weight unless otherwise noted or indicated. All % values are, unless otherwise noted, based on total amount of all ingredients used to synthesize or make the composition, which adds up to 100%. Any Markush group comprising a genus and subgenus therein includes the subgenus in the genus, e.g., in "R is hydrocarbyl or alkenyl," R may be alkenyl, alternatively R may be hydrocarbyl, which includes, among other subgenuses, alkenyl. For U.S. practice, all U.S. patent application publications and patents referenced herein, or a portion thereof if only the portion is referenced, are hereby incorporated herein by reference to the extent that incorporated subject matter does not conflict with the present description, which would control in any such conflict.

Aspects of the invention are described herein using various patent terms. For example, "alternatively" indicates a different and distinct embodiment. "Comparative example" means a non-invention experiment. "Comprises" and its variants (comprising, comprised of) are open ended. "Consists of" and its variants (consisting of) is closed ended. "Contacting" means bringing into physical contact. "May" confers a choice, not an imperative. "Optionally" means is absent, alternatively is present.

Aspects of the invention are described herein using various chemical terms. The meanings of said terms correspond to their definitions promulgated by IUPAC unless otherwise defined herein. For convenience, certain chemical terms are defined.

The term "aluminum hydride" means an agent for reducing halosilanes, the agent comprising at least one aluminum-hydrogen or aluminum-deuterium functional group.

The term "composition" means chemical matter that may be defined by an empirical formula of its constituent elements.

The term "deposition" is a process of generating, on a specific place, condensed matter. The condensed matter may or may not be restricted in dimension. Examples of deposition are film-forming, rod-forming, and particle-forming depositions.

The term "film" means a material that is restricted in one dimension. The restricted dimension may be characterized as "thickness" and as the dimension that, all other things being equal, increases with increasing length of time of a process of depositing said material to form the film.

The term "halogen" means fluorine, chlorine, bromine or iodine, unless otherwise defined.

The term "IUPAC" refers to the International Union of Pure and Applied Chemistry.

The term "lack" means free of or a complete absence of.

"Periodic Table of the Elements" means the version published 2011 by IUPAC.

The term "purify" means to increase concentration of a desired ingredient (up to ≤100%); alternatively to decrease concentration of one or more undesired ingredients (down to ≥0%), whether or not concentration of the desired ingredient has been increased; alternatively both.

The term "reaction by-product" means a secondary product of a chemical transformation of one or more reactants.

The term "remainder" means a portion that is left behind, e.g., a pot residue after a distillation.

The term "rod" means a material restricted in two dimensions, e.g., having an aspect ratio >2.

The term "separate" means to cause to physically move apart, and thus as a result be no longer in direct touching.

The term "silicon-yielding precursor" means a substance or molecule containing atoms of element 14 and being useful as a source of silicon in a deposition method. Examples of such deposition methods are described later.

The term "substrate" means a physical support having at least one surface upon which another material may be hosted.

The term "vehicle" means a material acting as a carrier, hosting medium, or solvent for another material, which may or may not be soluble therein. The vehicle may be a liquid.

The term "main group element" means an element in groups from 1,2, and 12 through 17 of the Periodic Table of the Elements.

The term "main group element catalyst" means a compound containing a main group element of the Periodic Table of the Elements or the elemental form of a main group element of the Periodic Table of the Elements that functions to accelerate the rate of reaction of the claimed compounds.

An aspect of the invention is the compound of formula (I):

$$(R^1R^2N)Si_nH_{2n}(NR^3R^4) \quad (I)$$

wherein subscript n is an integer from 3 to 9; $R^1$ is methyl, propyl, butyl, pentyl, hexyl, $(C_3$-$C_6)$cycloalkyl, $(C_2$-$C_6)$alkenyl, $(C_2$-$C_6)$alkynyl, or phenyl, and each $R^2$, $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ is H and each of $R^2$, $R^3$, and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^3$ are H and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be —$R^{1a}$—$R^{2a}$— wherein —$R^{1a}$—$R^{2a}$— is $(C_2-C_5)$alkylene and each $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be —$R^{1a}$—$R^{2a}$— wherein —$R^{1a}$—$R^{2a}$— is $(C_2-C_5)$alkylene and $R^3$ and $R^4$ are bonded together to be —$R^{3a}$—$R^{4a}$— wherein —$R^{3a}$—$R^{4a}$— is $(C_2-C_5)$alkylene; or $R^1$ and $R^3$ are bonded together to be —$R^{1a}$—$R^{3a}$— wherein —$R^{1a}$—$R^{3a}$— is $(C_2-C_5)$alkylene and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; and the $R^1R^2N$— and —$NR^3R^4$ groups are bonded to a same silicon atom or to different silicon atoms in the compound of formula (I).

In some aspects the compound of formula (I) may be further defined by the number, n, of its silicon atoms. In some aspects n is 3 or 4, alternatively n is 3 or 5, alternatively n is 4 or 5, alternatively n is 3, alternatively n is 4, alternatively n is 5, alternatively n is 6, alternatively n is 7, alternatively n is 8, alternatively n is 9.

Compounds of formula (I) having different values for n may differ from each other in at least one property, function, and/or use. It is believed that when n is 3, the compound of formula (I) may have higher vapor pressure than when n=4 or 5, all other things being equal. It is believed that when n is 4, the compound of formula (I) may have an intermediate vapor pressure than when n=3 or 5, all other things being equal. It is believed that when n is 5, the compound of formula (I) may have a lower vapor pressure than when n=3 or 4, all other things being equal.

The compound of formula (I) may be characterizable by a Si/N molar ratio. When n is 3, the Si/N molar ratio is 1.5; when n is 4, the molar Si/N ratio is 2; and when n is 5, the molar Si/N ratio is 2.5. Compounds of formula (I) having different values for the Si/N molar ratio may differ from each other in at least one property, function, and/or use. It is believed that when the Si/N molar ratio is 1.5, the compound of formula (I) may have higher vapor pressure and/or provide more SiN than when n=4 or 5, all other things being equal. It is believed that when the Si/N molar ratio is 2, the compound of formula (I) may have an intermediate vapor pressure and or provide an intermediate amount of SiN than when n=3 or 5, all other things being equal. It is believed that when the Si/N molar ratio is 2.5, the compound of formula (I) may have a lower vapor pressure or provide less SiN than when n=3 or 4, all other things being equal.

In some aspects the compound of formula (I) may be further defined by the compositional and/or structural nature of the $R^1R^2N$— group and/or the —$NR^3R^4$ group. The $R^1R^2N$— group may be an acyclic amino, alternatively the $R^1R^2N$— group is a cyclic amino. The —$NR^3R^4$ group may be an acyclic amino, alternatively the —$NR^3R^4$ group is a cyclic amino. Each $R^1R^2N$— group and —$NR^3R^4$ group independently may be an acyclic amino, alternatively each $R^1R^2N$— group and —$NR^3R^4$ group independently may be a cyclic amino, alternatively the $R^1R^2N$— group may be an acyclic amino and the —$NR^3R^4$ group independently may be a cyclic amino, or vice versa.

Compounds of formula (I) having different chains in the $R^1R^2N$— groups and/or the —$NR^3R^4$ groups may differ from each other in at least one property, function, and/or use.

It is believed that when the $R^1R^2N$— and/or —$NR^3R^4$ group is acyclic amino (i.e., open chain), the compound of formula (I) may have higher vapor pressure than when $R^1R^2N$— group is cyclic amino. It is believed that when the $R^1R^2N$— and/or —$NR^3R^4$ group is cyclic amino (i.e., cyclic chain), the compound of formula (I) may have lower vapor pressure than when $R^1R^2N$— is acyclic amino.

In some aspects of the compound of formula (I) wherein the $R^1R^2N$— group is acyclic amino, the nature of $R^1$, $R^2$, or both $R^1$ and $R^2$, may be further defined. In some aspects of the compound of formula (I) $R^1$ is methyl, propyl, butyl, pentyl, hexyl, $(C_3-C_6)$cycloalkyl, $(C_2-C_6)$alkenyl, $(C_2-C_6)$alkynyl, or phenyl and $R^2$ is $(C_1-C_6)$alkyl; alternatively $R^1$ is methyl, propyl, butyl, pentyl, hexyl, $(C_3-C_6)$cycloalkyl, $(C_2-C_6)$alkenyl, $(C_2-C_6)$alkynyl, or phenyl and $R^2$ is $(C_3-C_5)$alkyl; alternatively $R^1$ is methyl, propyl, butyl, pentyl, hexyl, $(C_3-C_6)$cycloalkyl, $(C_2-C_6)$alkenyl, $(C_2-C_6)$alkynyl, or phenyl and $R^2$ is isopropyl or a secondary or tertiary $(C_4-C_5)$ alkyl; alternatively $R^1$ is methyl and $R^2$ is isopropyl, sec-butyl, iso-butyl, or tert-butyl; alternatively $R^1$ is propyl and $R^2$ is isopropyl, sec-butyl, iso-butyl, or tert-butyl; alternatively each $R^1$ and $R^2$ independently is isopropyl, sec-butyl, iso-butyl, or tert-butyl; alternatively $R^1$ is methyl and $R^2$ is tert-butyl; alternatively each $R^1$ and $R^2$ independently is $(C_3-C_4)$alkyl; alternatively each $R^1$ and $R^2$ is isopropyl; alternatively each $R^1$ and $R^2$ is sec-butyl; alternatively $R^1$ is $(C_3-C_6)$cycloalkyl and $R^2$ is as defined in any one of the above aspects; alternatively $R^1$ is $(C_2-C_6)$alkenyl and $R^2$ is as defined in any one of the above aspects; alternatively $R^1$ is $(C_2-C_6)$alkynyl and $R^2$ is as defined in any one of the above aspects; alternatively $R^1$ is H and $R^2$, $R^3$ and $R^4$ independently is as defined in any one of the above aspects; alternatively each of $R^1$ and $R^3$ are H and each of $R^2$ and $R^4$ independently is as defined in any one of the above aspects; alternatively $R^1$ is phenyl and $R^2$ is as defined in any one of the above aspects; alternatively $R^1$ is $(C_3-C_6)$cycloalkyl, $(C_2-C_6)$alkenyl, $(C_2-C_6)$alkynyl, or phenyl, and $R^2$ is $(C_1-C_6)$alkyl; alternatively $R^2$ is the same as $R^1$; alternatively $R^1$ is the same as $R^3$ and $R^2$ is the same as $R^4$; alternatively $R^1$ is the same as $R^2$ and $R^3$ is the same as $R^4$.

Compounds of formula (I) having different composition of $R^1$ and $R^2$ in the acyclic or open chain $R^1R^2N$— group may differ from each other in at least one property, function, and/or use. It is believed that when at least one of $R^1$ and $R^2$ group is $(C_3-C_6)$alkyl the compound of formula (I) may have improved stability. It is believed that when the $R^1$ is methyl, propyl, butyl, pentyl, or hexyl and/or $R^2$ group is $(C_1-C_6)$alkyl the compound of formula (I) may be made from more cost effective starting materials. It is believed that when the $R^1$ and/or $R^2$ group is $(C_2-C_6)$alkenyl the compound of formula (I) may have a favorable basicity, especially when the carbon-carbon double bond of the $(C_2-C_6)$alkenyl is conjugated with the lone electron pair on the N atom in formula (I). It is believed that when the $R^1$ and/or $R^2$ group is $(C_2-C_6)$alkynyl the compound of formula (I) may have a more desirable molecular geometry. It is believed that when the $R^1$ and/or $R^2$ group is phenyl the compound of formula (I) may have a desirable photochemical property. The foregoing benefits may enable an improved silicon material deposition process such as a chemical vapor deposition (CVD) and/or atomic layer deposition (ALD) process.

In some aspects of the compound of formula (I) wherein the $R^1R^2N$— group is cyclic amino, the nature of —$R^{1a}$—$R^{2a}$— may be further defined. In the compound of formula (I) $R^1$ and $R^2$ may be bonded together to be —$R^{1a}$—$R^{2a}$— wherein —$R^{1a}$—$R^{2a}$— is $(C_3-C_5)$alkylene; alternatively —$R^{1a}$—$R^{2a}$— is $(C_4$ or $C_5)$alkylene.

Compounds of formula (I) having different composition of —$R^{1a}$—$R^{2a}$— in the closed chain $R^1R^2N$— group may differ from each other in at least one property, function, and/or use. It is believed that when the —$R^{1a}$—$R^{2a}$— is ($C_3$-$C_5$)alkylene the compound of formula (I) may have a desirable reactivity for depositing Si-containing films.

In some aspects of the compound of formula (I) wherein the —$NR^3R^4$ group is acyclic amino, the nature of $R^3$, $R^4$, or both $R^3$ and $R^4$, may be further defined. In some aspects of the compound of formula (I) each $R^3$ and $R^4$ independently is ($C_1$-$C_6$)alkyl; alternatively $R^3$ is ($C_1$-$C_6$)alkyl and $R^4$ is ($C_3$-$C_5$)alkyl; alternatively $R^3$ is ($C_1$-$C_6$)alkyl and $R^4$ is isopropyl or a secondary or tertiary ($C_4$-$C_5$)alkyl; alternatively $R^3$ is methyl or ethyl and $R^4$ is isopropyl, sec-butyl, iso-butyl, or tert-butyl; alternatively $R^3$ is methyl and $R^4$ is isopropyl, sec-butyl, iso-butyl, or tert-butyl; alternatively each $R^3$ and $R^4$ independently is isopropyl, sec-butyl, iso-butyl, or tert-butyl; alternatively $R^3$ is methyl and $R^4$ is tert-butyl; alternatively each $R^3$ and $R^4$ independently is ($C_3$-$C_4$)alkyl; alternatively each $R^3$ and $R^4$ is isopropyl; alternatively each $R^3$ and $R^4$ is sec-butyl; alternatively $R^3$ is ($C_3$-$C_6$)cycloalkyl and $R^4$ is as defined in any one of the above aspects; alternatively $R^3$ is ($C_2$-$C_6$)alkenyl and $R^4$ is as defined in any one of the above aspects; alternatively $R^3$ is ($C_2$-$C_6$)alkynyl and $R^4$ is as defined in any one of the above aspects; alternatively $R^3$ is H and $R^4$ is as defined in any one of the above aspects; alternatively $R^3$ is phenyl and $R^4$ is as defined in any one of the above aspects; alternatively $R^3$ is ($C_3$-$C_6$)cycloalkyl, ($C_2$-$C_6$)alkenyl, ($C_2$-$C_6$)alkynyl, or phenyl, and $R^4$ is ($C_1$-$C_6$)alkyl; alternatively each of $R^1$ and $R^3$ are H and each of $R^2$ and $R^4$ independently is as defined in any one of the above aspects; alternatively $R^4$ is the same as $R^3$; alternatively $R^3$ is the same as $R^1$ and $R^4$ is the same as $R^2$; alternatively $R^1$ is the same as $R^2$ and $R^3$ is the same as $R^4$.

Compounds of formula (I) having different composition of $R^3$ and $R^4$ in the open chain —$NR^3R^4$ group may differ from each other in at least one property, function, and/or use. It is believed that when at least one of $R^3$ and $R^4$ group is ($C_3$-$C_6$)alkyl the compound of formula (I) may have improved stability. It is believed that when the $R^3$ and/or $R^4$ group is ($C_1$-$C_6$)alkyl the compound of formula (I) may be made from more cost effective starting materials. It is believed that when the $R^3$ and/or $R^4$ group is ($C_2$-$C_6$)alkenyl the compound of formula (I) may have a favorable basicity, especially when the carbon-carbon double bond of the ($C_2$-$C_6$)alkenyl is conjugated with the lone electron pair on the N atom in formula (I). It is believed that when the $R^3$ and/or $R^4$ group is ($C_2$-$C_6$)alkynyl the compound of formula (I) may have a more desirable molecular geometry. It is believed that when the $R^3$ and/or $R^4$ group is phenyl the compound of formula (I) may have a desirable photochemical property. The foregoing benefits may enable an improved silicon material deposition process such as a chemical vapor deposition (CVD) and/or atomic layer deposition (ALD) process.

In some aspects of the compound of formula (I) wherein the —$NR^3R^4$ group is cyclic amino, the nature of —$R^{3a}$—$R^{4a}$— may be further defined. In the compound of formula (I) $R^3$ and $R^4$ may be bonded together to be —$R^{3a}$—$R^{4a}$— wherein —$R^{3a}$—$R^{4a}$— is ($C_3$-$C_5$)alkylene; alternatively —$R^{3a}$—$R^{4a}$— is ($C_4$ or $C_5$)alkylene.

Compounds of formula (I) having different composition of —$R^{3a}$—$R^{4a}$— in the closed chain —$NR^3R^4$ group may differ from each other in at least one property, function, and/or use. It is believed that when the —$R^{3a}$—$R^{4a}$— is ($C_3$-$C_5$)alkylene the compound of formula (I) may have a desirable reactivity for depositing Si-containing films.

In some aspects the compound of formula (I) may be further defined by whether the $R^1R^2N$— group and the —$NR^3R^4$ group are bonded to the same silicon atom or to different silicon atoms in the compound of formula (I). The $R^1R^2N$— and —$NR^3R^4$ groups may be bonded to the same silicon atom in the compound of formula (I). Alternatively, the $R^1R^2N$— and —$NR^3R^4$ groups may be bonded to different silicon atoms in the compound of formula (I). It is believed that when the $R^1R^2N$— and —$NR^3R^4$ groups are bonded to the same silicon atom in the compound of formula (I) the compound may be used to end-cap surface reactive groups on a surface of a substrate It is believed that when the $R^1R^2N$— and —$NR^3R^4$ groups are bonded to different silicon atoms in the compound of formula (I) the compound may be used to connect or crosslink different surface reactive groups on a surface of a substrate.

In some aspects the compound of formula (I) may be further defined by its regioisomeric structure when the $R^1R^2N$— and —$NR^3R^4$ groups are bonded to different silicon atoms in the compound of formula (I). In said aspects the compound of formula (I) may be a compound of formula (I-a) $R^1R^2N$—$SiH_2SiH_2SiH_2NR^3R^4$ (I-a), alternatively a compound of formula (I-b) $R^1R^2N$—$SiH(SiH_3)SiH_2NR^3R^4$ (I-b), alternatively a compound of formula (I-c) $R^1R^2N$—$SiH_2SiH_2SiH_2SiH_2NR^3R^4$ (I-c), alternatively a compound of formula (I-d) $R^1R^2N$—$SiH(SiH_3)SiH_2SiH_2NR^3R^4$ (I-d), alternatively a compound of formula (I-e) $R^1R^2N$—$SiH_2SiH(SiH_3)SiH_2NR^3R^4$ (I-e), alternatively a compound of formula (I-f) $R^1R^2N$—$Si(SiH_3)_2SiH_2NR^3R^4$ (I-f), alternatively a compound of formula (I-g) $R^1R^2N$—$SiH_2SiH_2SiH_2SiH_2SiH_2NR^3R^4$ (I-g), alternatively a compound of formula (I-h) $R^1R^2N$—$SiH(SiH_3)SiH_2SiH_2SiH_2NR^3R^4$ (I-h), alternatively a compound of formula (I-i) $R^1R^2N$—$SiH_2SiH(SiH_3)SiH_2SiH_2NR^3R^4$ (I-i), alternatively a compound of formula (I-j) $R^1R^2N$—$SiH_2SiH_2SiH(SiH_3)SiH_2NR^3R^4$ (I-j), alternatively a compound of formula (I-k) $R^1R^2N$—$SiH(SiH_2SiH_3)SiH_2SiH_2NR^3R^4$ (I-k), alternatively a compound of formula (I-l) $R^1R^2N$—$SiH_2Si(SiH_3)_2SiH_2NR^3R^4$ (I-l); all wherein $R^1$, $R^2$, $R^3$ and $R^4$ are as defined in any one of the above aspects. Alternatively, the compound of formula (I) may be an alpha,omega compound wherein the $R^1R^2N$— and —$NR^3R^4$ groups are bonded to different terminal silicon atoms of a compound of formula (I-m): $R^1R^2N$—$(SiH_2)_n$—$NR^3R^4$ (I-m), wherein n, $R^1$, $R^2$, $R^3$ and $R^4$ are as defined in any one of the above aspects.

In some aspects the compound of formula (I) may be further defined by its regioisomeric structure when the $R^1R^2N$— and —$NR^3R^4$ groups are bonded to a same silicon atom in the compound of formula (I). In said aspects the compound of formula (I) may be a compound of formula (I-aa) $R^1R^2N$—$SiH(NR^3R^4)SiH_2SiH_3$ (I-aa), alternatively a compound of formula (I-bb) $R^1R^2N$—$Si(NR^3R^4)(SiH_3)SiH_3$ (I-bb), alternatively a compound of formula (I-cc) $R^1R^2N$—$SiH(NR^3R^4)SiH_2SiH_2SiH_3$ (I-cc), alternatively a compound of formula (I-dd) $R^1R^2N$—$Si(NR^3R^4)(SiH_3)SiH_2SiH_3$ (I-dd), alternatively a compound of formula (I-ee) $R^1R^2N$—$SiH(NR^3R^4)SiH(SiH_3)SiH_3$ (I-ee), alternatively a compound of formula (I-ff) $R^1R^2N$—$SiH(NR^3R^4)SiH_2SiH_2SiH_2SiH_3$ (I-ff), alternatively a compound of formula (I-gg) $R^1R^2N$—$Si(NR^3R^4)(SiH_3)SiH_2SiH_2SiH_3$ (I-gg), alternatively a compound of formula (I-hh) $R^1R^2N$—$SiH(NR^3R^4)SiH(SiH_3)SiH_2SiH_3$ (I-hh), alternatively a compound of formula (I-ii) $R^1R^2N$—$SiH(NR^3R^4)SiH_2SiH(SiH_3)SiH_3$ (I-ii), alternatively a compound of formula (I-jj)

$R^1R^2N$—Si(NR$^3$R$^4$)(SiH$_2$SiH$_3$)SiH$_2$SiH$_3$ (I-jj), alternatively a compound of formula (I-kk) $R^1R^2N$—SiH(NR$^3$R$^4$)Si(SiH$_3$)$_2$SiH$_3$ (I-kk); all wherein $R^1$, $R^2$, $R^3$ and $R^4$ are as defined in any one of the above aspects.

Compounds of formula (I) having different substructures may differ from each other in at least one property, function, and/or use. Each of the different compounds of formulas (I-a) to (I-m) and (I-aa) to (I-kk) has unique properties such as a unique molecular symmetry, molecular dipole moment and chemical bonding characteristics. These unique properties affect physisorption and chemisorption of the substructure on a substrate surface in deposition processes such as CVD or ALD processes.

In some aspects the compound of formula (I) is any one of the following species: 1,1-bis(diisopropylamino)trisilane; 1,2-bis(diisopropylamino)trisilane; 1,3-bis(diisopropylamino)trisilane; 2,2-bis(diisopropylamino)trisilane; 1,2-bis(diisopropylamino)tetrasilane; 1,3-bis(diisopropylamino)tetrasilane; 1,4-bis(diisopropylamino)tetrasilane; 1,5-bis(diisopropylamino)pentasilane; 1,3-bis(diisopropylamino)-2,2-bissilyltrisilane; and 1,1-bis(diisopropylamino)-2,2-bissilyltrisilane. For example, the compound of formula (I) may be 1,1-bis(diisopropylamino)trisilane; alternatively 1,2-bis(diisopropylamino)trisilane; alternatively 1,3-bis(diisopropylamino)trisilane; alternatively 2,2-bis(diisopropylamino)trisilane; alternatively 1,2-bis(diisopropylamino)tetrasilane; alternatively 1,3-bis(diisopropylamino)tetrasilane; alternatively 1,4-bis(diisopropylamino)tetrasilane; alternatively 1,5-bis(diisopropylamino)pentasilane; alternatively 1,3-bis(diisopropylamino)-2,2-bissilyltrisilane; alternatively 1,1-bis(diisopropylamino)-2,2-bissilyltrisilane. Alternatively, the compound of formula (I) may be a combination of any two or more of the foregoing species. Alternatively, any one of the foregoing species may be omitted and the compound of formula (I) may be selected from the group consisting of the remaining nine species. Alternatively, any 1 to 10 of the foregoing species may be omitted from formula (I) and the compound of formula (I) may be selected from the group consisting of the remaining species.

In some aspects the compound of formula (I) may be further defined as being any one of the species thereof described later in the working examples. Compounds of formula (I) having different structures may differ from each other in at least one property, function, and/or use. It is believed that all compounds of formula (I), including the species of the working examples, may have the aforementioned desirable vapor pressures and chemical reactivities for depositing Si-containing films.

In some aspects the compound of formula (I) may be further defined by its isotopic composition. The compound of formula (I) may be a natural abundance isotope form, alternatively an isotopically-enriched form, alternatively a mixture of said forms. The isotopically-enriched forms of the compound of formula (I) include forms that contain a greater-than-natural-abundance amount of deuterium, tritium, $^{29}$Si, $^{30}$Si, $^{32}$Si, or a combination of any two or more thereof. In addition to the uses of the compound of formula (I) described herein, isotopically-enriched forms of the compound of formula (I) may be useful in applications wherein detection of the isotopically-enriched compound of formula (I) or an isotopically-enriched silicon material (e.g., film) made therefrom would be helpful. Examples of such applications are medical research and anti-counterfeiting applications. Compounds of formula (I) having different isotopic compositions may differ from each other in at least one property, function, and/or use.

The compound of formula (I) may be stored under an anhydrous condition (i.e., lacking water), under an inert atmosphere, or, typically, both, i.e., anhydrous inert atmosphere. The inert atmosphere may be a gas of molecular nitrogen, helium, argon, or a mixture of any two or more thereof. Compounds of formula (I) having different concentrations of water may differ from each other in at least one property, function, and/or use.

Another aspect of the invention is the composition comprising the compound of formula (I) and at least one additional ingredient that is different than the compound of formula (I). Each additional ingredient independently may independently differ from the compound of formula (I) in function, composition, or structure.

In some aspects the composition may be further defined by the number of the compounds of formula (I) contained therein. In some aspects the composition contains only one compound of formula (I), alternatively the composition contains only two different compounds of formula (I), alternatively the composition contains only three different compounds of formula (I), alternatively the composition contains only four different compounds of formula (I), alternatively the composition contains five different compounds of formula (I).

Compositions having different numbers of compounds of formula (I) may differ from each other in at least one property, function, and/or use. It is believed that the composition containing only 1 compound of formula (I) may have an exact or narrow boiling point under ambient pressure and enable a uniform temperature for distillation or reaction thereof and provide fewer reaction by-products. It is believed that the composition containing only 2 to 5 different compounds of formula (I) may boil over a range of temperatures under ambient pressure and provide different reactivity or enhance silicon material film performance than when there is only 1 such compound.

In some aspects the composition may be further defined by the compositional and/or structural nature of the compound of formula (I) contained therein. In some aspects, the composition comprises a compound of formula (I) of any one of the above-defined aspects thereof. Compositions having different compositional and/or structural nature of compound of formula (I) may differ from each other in at least one property, function, and/or use. The compositions having the compounds of formula (I-a) to (I-m) and (I-aa) to (I-kk) may provide desirable film deposition rate and properties.

In some aspects the composition may be further defined by the number of the at least one additional ingredient contained therein that is different than the compound of formula (I). In some aspects the composition contains only one additional ingredient that is not a compound of formula (I), alternatively the composition contains only two different additional ingredients that are not compounds of formula (I), alternatively the composition contains only three different additional ingredients that are not compounds of formula (I), alternatively the composition contains only four different additional ingredients that are not compounds of formula (I), alternatively the composition contains only five different additional ingredients that are not compounds of formula (I), alternatively the composition contains six or more additional ingredients that are not compound of formula (I). Compositions having different numbers of the at least one additional ingredient may differ from each other in at least one property, function, and/or use.

In some aspects the composition may be further defined by the compositional and/or structural nature of the at least one additional ingredient contained therein that is not a compound of formula (I). Each additional ingredient independently may be a covalently bonded substance (i.e., not a salt), which independently may be a solid, liquid, or gas; alternatively a solid (e.g., one or more $Si_{80}$ precursors); alternatively a gas (e.g., monosilane and/or disilane dissolved in the compound of formula (I)); alternatively a liquid (e.g., trisilane, tetrasilane, or pentasilane). Each solid additional ingredient, when present, independently may be dissolved, alternatively suspended in the compound of formula (I). Each liquid additional ingredient, when present, independently may have a boiling point at 101.3 kPa of from 30° to 350° C., alternatively from 30° to 250° C., alternatively from 50° to 90° C., alternatively from 90° to 134° C., alternatively from 135° to 250° C. Each solid or liquid additional ingredient independently may comprise Si atoms, alternatively lack Si atoms.

In some aspects, the at least one additional ingredient may be a silane that is different than the compound of formula (I). The silane may have from 1 to 9 silicon atoms, hydrogen and/or halogen atoms, and lack a nitrogen atom; alternatively the silane may have from 1 to 9 silicon atoms, hydrogen and/or halogen atoms, and lack nitrogen and oxygen atoms; alternatively the silane may consist of from 1 to 9 silicon atoms and halogen atoms; alternatively the silane may have 1 or 2 silicon atoms, hydrogen atoms, and a nitrogen atom. The silane that is not a compound of formula (I) may have n−1 silicon atoms, alternatively n−2 silicon atoms, alternatively 2n silicon atoms, alternatively 2n−1 silicon atoms, all wherein n is as defined in any one of the above aspects for the compound of formula (I); alternatively the silane that is not a compound of formula (I) may have 1 or 2 silicon atoms; alternatively from 3 to 9 silicon atoms; alternatively 1 silicon atom, alternatively 2 silicon atoms, alternatively 3 silicon atoms, alternatively 4 silicon atoms, alternatively 5 silicon atoms, alternatively 6 silicon atoms, alternatively 7 silicon atoms, alternatively 8 silicon atoms, alternatively 9 silicon atoms. The silane that is not a compound of formula (I) may consist of Si and H atoms; alternatively may consist of Si, H, and nitrogen atoms; alternatively may consist of Si, H, and halogen atoms selected from Cl, Br, and I; alternatively may consist of Si and halogen atoms selected from Cl, Br, and I.

In the composition at least one, alternatively each additional ingredient independently may comprise a silicon-yielding precursor other than compound of formula (I) (e.g., a hydridosilane such as monosilane, disilane, trisilane, tetrasilane, pentasilane, hexasilane, heptasilane, octasilane, or nonasilane; or an organosilicon such as an organosilane such as trimethyl- or tetramethyl-monosilane, dichlorodimethyl-monosilane, or chlorotrimethyl-monosilane, or a silaalkane such as 1,3-disilabutane); alternatively an aminosilane or am inodisilane such as diisopropylaminosilane or diisopropylaminodisilane, respectively; alternatively an organic precursor lacking silicon (e.g., an alkane such as methane, including natural gas; carbon tetrachloride; propane; hexane; or a mixture of any two or more thereof), alternatively an inorganic precursor lacking silicon (e.g., anhydrous ammonia, molecular nitrogen, hydrazine, molecular oxygen, ozone, nitrous oxide, water, or hydrogen peroxide), alternatively a mixture thereof. Additionally or alternatively, the additional precursor may be a source of carbon comprising a carbon-containing precursor (e.g., the organosilicon), a source of oxygen comprising an oxygen-containing precursor (e.g., molecular oxygen, ozone, nitrous oxide, water, or hydrogen peroxide), or a source of nitrogen comprising nitrogen-containing precursor (e.g., anhydrous ammonia, molecular nitrogen, or hydrazine), or a combination of any two or more of the source of carbon comprising a carbon-containing precursor, the source of oxygen comprising an oxygen-containing precursor, and the source of nitrogen comprising nitrogen-containing precursor. The additional precursor may function as a solvent for the compound of formula (I), or vice versa, in the composition. The composition that comprises the compound of formula (I) and an additional ingredient that contains C or N or O or S may help to deliver the compound of formula (I) to a film-forming reactor or help convert the compound of formula (I) to a desirable silicon film.

Alternatively, in the composition the at least one additional ingredient may be a solvent or carrier gas for a precursor such as a solvent or carrier gas for the compound of formula (I). The carrier gas may be a noble gas such as a gas of He or Ar. The solvent may be an organic solvent lacking Si. The organic solvent may also function as a source of carbon-containing precursor; alternatively the source of carbon-containing precursor may also function as an organic solvent in the composition.

Alternatively, the composition may consist essentially of the compound of formula (I) and the silane that is not a compound of formula (I). The composition that consists essentially of the compound of formula (I) and the silane that is not a compound of formula (I) lacks halosilanes, alternatively lacks any silane containing nitrogen that is not a compound of formula (I), alternatively lacks any silane containing halogen and nitrogen; but otherwise the composition may contain additional ingredients, e.g., an organic solvent, inert gas or a perhydridosilane, which consists of Si and H atoms. It is believed that the composition that consists essentially of the compound of formula (I) and the silane that is not a compound of formula (I) may allow higher film deposition rates or film deposition selectivity.

Alternatively, the composition may consist of the compound of formula (I) and at least one silane that is not a compound of formula (I). The composition that consists of the compound of formula (I) and the at least one silane that is not a compound of formula (I) may lack any other Si-containing substance.

Compositions having different compositional and/or structural nature of the at least one additional ingredient may differ from each other in at least one property, function, and/or use.

Another aspect of the invention is the method of making a compound of formula (I), the method comprising:
contacting the compound of formula (c1): $(R^1R^2N)Si_nX_{2n}(NR^3R^4)$ (c1), wherein each X independently is a halogen atom selected from Cl, Br, and I; and n, $R^1$, $R^2$, $R^3$, and $R^4$ are is defined in any one of the above aspects of formula (I), with an aluminum hydride to give a mixture of the compound of formula (I) and at least one reaction by-product. This contacting step may be referred to for convenience herein as a reduction contacting step.

In some aspects the method of making the compound of formula (I) may be further defined by the nature of the halogen, X. In some aspects, at least one X is Cl; alternatively at least one X is Br; alternatively at least one X is I; alternatively X is Cl or Br; alternatively X is Br or I; alternatively X is Cl; alternatively X is Br; alternatively X is I. The methods having different compositions for X may differ from each other in at least one result, property, function, and/or use. The ease of reducing the Si—X bond to Si—H may increase from X═Cl to X═Br to X═I.

In some aspects the method of making the compound of formula (I) may be further defined by the nature of the aluminum hydride. The aluminum hydride may be an alkylaluminum hydride of formula $AlR_xH_{3-x}$ or $AlR_xD_{3-x}$, wherein Al is aluminum; x is 1 or 2; each R independently is a $(C_1-C_6)$alkyl, a $(C_7-C_{12})$alkyl, a $(C_{13}-C_{20})$alkyl, or a $(C_{21}-C_{40})$alkyl; H is a hydrogen atom; and D is a deuterium atom. Examples of the alkylaluminum hydride of formula $AlR_xH_{3-x}$ are methylaluminum dihydride; dimethylaluminum hydride; a mixture of methylaluminum dihydride and dimethylaluminum hydride; ethylaluminum dihydride; diethylaluminum hydride; a mixture of ethylaluminum dihydride and diethylaluminum hydride; isobutylaluminum dihydride; diisobutylaluminum hydride; and a mixture of isobutylaluminum dihydride and diisobutylaluminum hydride. Diisobutylaluminum hydride is commonly abbreviated as DIBAL and is believed to exist as a dimer of formula $C_{16}H_{38}Al_2$. Examples of the alkylaluminum hydride of formula $AlR_xD_{3-x}$ are methylaluminum dideuteride; dimethylaluminum deuteride; a mixture of methylaluminum dideuteride and dimethylaluminum deuteride; ethylaluminum dideuteride; diethylaluminum deuteride; a mixture of ethylaluminum dideuteride and diethylaluminum deuteride; isobutylaluminum dideuteride; diisobutylaluminum deuteride; and a mixture of isobutylaluminum dideuteride and diisobutylaluminum deuteride.

Alternatively the aluminum hydride may be a Group II metal aluminum hydride of formula $M(AlH_4)_2$ or $M(AlD_4)_2$, wherein M is the Group II metal and each H is a hydrogen atom, and D is a deuterium atom. Examples of the Group II metal aluminum hydride are magnesium aluminum hydride and calcium aluminum hydride.

Alternatively the aluminum hydride may be a Group I metal aluminum hydride of formula $MAlH_4$ or $MAlD_4$, wherein M is the Group I metal, H is a hydrogen atom, and D is a deuterium atom. The Group I metal may be Li, Na, or K. Examples of the Group I metal aluminum hydride are $KAlH_4$, $NaAlH_4$, $LiAlH_4$, $KAlD_4$, $NaAlD_4$, and $LiAlD_4$. The Group I metal aluminum hydride may be $KAlH_4$, $NaAlH_4$, or $LiAlH_4$; alternatively $NaAlH_4$ or $LiAlH_4$; alternatively $KAlH_4$; alternatively $NaAlH_4$; alternatively $LiAlH_4$; alternatively $KAlD_4$, $NaAlD_4$, or $LiAlD_4$; alternatively $NaAlD_4$ or $LiAlD_4$; alternatively $KAlD_4$; alternatively $NaAlD_4$; alternatively $LiAlD_4$.

Alternatively, the aluminum hydride may be a combination of any two or more of the aforementioned examples. E.g., the aluminum hydride may be a combination of diisobutylaluminum hydride and $LiAlH_4$. Typically the aluminum hydride is at least $LiAlH_4$.

The methods having different compositions for aluminum hydride may differ from each other in at least one result, property, function, and/or use. Different compositions of aluminum hydrides may provide different reduction selectivities.

In some embodiments, the aluminum hydride does not further comprise a complexing agent. In other embodiments the aluminum hydride further comprises a complexing agent, which would form a dative bond to Al. The complexing agent may be an aprotic compound containing O, N or S, such as an alkyl ether (e.g., diethyl ether), oxacycloalkane (e.g., tetrahydrofuran), or a trialkylamine (e.g., trimethylamine). The complexing agent may be used to enhance shelf stability, modulate reactivity, or the like, of the aluminum hydride. The complexing agent may be removed from the reaction mixture prior to performing the reduction contacting step. The complexed aluminum hydride may have improved reduction selectivity over uncomplexed aluminum hydride.

Aluminum hydrides suitable for use in the method are generally known. Suitable aluminum hydrides may be readily obtained from a commercial supplier such as Sigma-Aldrich Company (St. Louis, Mo., USA) and/or prepared by any suitable process such as the process of U.S. Pat. No. 2,765,329. In some embodiments, the aluminum hydride does not further comprise a trialkylaluminum. In other embodiments the aluminum hydride further comprises a trialkylaluminum. The manufacture of an alkylaluminum hydride may produce a mixture of the dialkylaluminum hydride and alkylaluminum dihydride, as well as a corresponding trialkylaluminum as a by-product, wherein in the trialkylaluminum the alkyl is the same as R in formula $AlR_xH_{3-x}$ or $AlR_xD_{3-x}$.

In some aspects the method of making the compound of formula (I) may be further defined by the nature of the halogen, X, in combination with the nature of the aluminum hydride. In some aspects of the method each X is Cl or Br and the aluminum hydride is $MAlH_4$, alternatively each X is Cl or Br and the aluminum hydride is $LiAlH_4$, alternatively each X is Br and the aluminum hydride is $LiAlH_4$, alternatively each X is Cl and the aluminum hydride is $LiAlH_4$. The methods having different compositions for X and for the aluminum hydride may differ from each other in at least one result, property, function, and/or use. The combination of X is Br and $LiAlH_4$ may give a higher yield of product than the combination of X is Cl and $LiAlH_4$.

In some aspects the method of making the compound of formula (I) may be further defined by the nature of the composition of the reaction mixture in the reduction contacting step. The reduction contacting step may lack a vehicle; alternatively the reduction contacting step may further comprise a vehicle, wherein the compound of formula (c1) and aluminum hydride are in admixture with the vehicle during the reduction contacting step. The vehicle may be an alkylene glycol dialkyl ether vehicle, wherein the compound of formula (c1) and aluminum hydride are in admixture with the alkylene glycol dialkyl ether vehicle during the reduction contacting step. The alkylene glycol dialkyl ether vehicle may function as a solvent for one or both of the compound of formula (c1) and aluminum hydride. The alkylene glycol dialkyl ether vehicle may have a boiling point that is at least 10° C., alternatively at least 30° C., alternatively at least 50° C. higher than the boiling point of the compound of formula (I).

The alkylene glycol dialkyl ether vehicle may consist of carbon, hydrogen and oxygen atoms or may be a halogenated alkylene glycol dialkyl ether vehicle consisting of carbon, hydrogen, oxygen, and halogen atoms. The alkylene glycol dialkyl ether may be a tetramethylene glycol di($C_1$-$C_4$)alkyl ether, propylene glycol di($C_2$-$C_4$)alkyl ether, ethylene glycol di($C_3$ or $C_4$)alkyl ether, or a combination of any two or more thereof. E.g., the alkylene glycol dialkyl ether may be tetramethylene glycol dimethyl ether, propylene glycol dipropyl ether, or ethylene glycol dibutyl ether. The halogenated alkylene glycol dialkyl ether vehicle may be a tetramethylene glycol halo-substituted di($C_1$-$C_4$)alkyl ether, propylene glycol halo-substituted di($C_2$-$C_4$)alkyl ether, ethylene glycol halo-substituted di($C_3$ or $C_4$)alkyl ether, or a combination of any two or more thereof. E.g., the halogenated alkylene glycol dialkyl ether may be tetramethylene glycol bis(trifluoromethyl) ether, propylene glycol bis(3,3,3-trifluoropropyl) ether, or ethylene glycol bis(3,3,3-trifluorobutyl) ether. The alkylene glycol dialkyl ether vehicle may be removed from the reaction mixture after completion of the reduction contacting step, alternatively the alkylene glycol dialkyl ether vehicle may be left in a remainder and the compound of formula (I) may be removed (e.g., distilled) from the remainder to separate it from the alkylene glycol dialkyl ether vehicle. The methods having different compositions for the alkylene glycol dialkyl ether vehicle may differ from each other in at least one result, property, function, and/or use. Different compositions of the alkylene glycol dialkyl ether may provide different solubility for the compound of formula (c1) and aluminum hydride reducing agent.

In some aspects the method of making the compound of formula (I) may be further defined by one or more optional preliminary steps that come before the reduction contacting step. The method may further comprise a preliminary step of making the compound of formula (c1). For example, the method may further comprise a preliminary step of contacting one molar equivalent of a compound of formula (a1): $R^1R^2NM$ (a1) and one molar equivalent of a compound of formula (a2): $R^3R^4NM$ (a2) with a compound of formula (b1): $Si_nX_{2n+2}$ (b1), or contacting one molar equivalent of a compound of formula (a3) $m(R^2)N—R^{1a}—R^{3a}—N(R^4)m$ (a3) with a compound of formula (b1), to give the compound of formula (c1), wherein each M independently is a Group I element selected from H, Li, Na, and K; and X, n, $R^1$, $R^2$, $R^3$, and $R^4$ are as defined in any one of the above aspects. This contacting step may be referred to for convenience herein as a substitution contacting step.

In some aspects the method of making the compound of formula (I) may be further defined by the nature of the Group I element in the optional substitution contacting step. The M may be H; alternatively M may be a Group I metal Li, Na, or K; alternatively M is Li or Na; alternatively M is Li or K; alternatively M is Na or K; alternatively M is Li; alternatively M is Na; alternatively M is K. The methods having different compositions for M may differ from each other in at least one result, property, function, and/or use. The compound of formula (a1): $R^1R^2NM$ (a1) may be prepared from $R^1R^2NH$ and an organometallic base wherein the metal is M. The compound of formula (a2): $R^3R^4NM$ (a2) may be prepared from $R^3R^4NH$ and an organometallic base wherein the metal is M.

In some aspects the method of making the compound of formula (I) may further comprise an additional preliminary step of synthesizing the compound of formula (b1): $Si_nX_{2n+2}$ (b1). The compound of formula (b1) may be made and purified with any suitable method, including a known method. For instance, it may be made by chlorination of elemental silicon, dephenylation of phenylsilanes with hydrogen halides, or disproportionation, redistribution or decomposition of other compounds of formula (b1). These reactions usually yield mixtures of different isomers. The isomers can be separated from each other with any suitable separation technique, including known methods comprising distillation, sublimation and/or crystallization. Any particular isomer of the compound of formula (b1) tends to retain its silicon atom backbone structure when it is converted to the compound of formula (c1), which in turn retains the same silicon atom backbone structure when it is converted to the compound of formula (I), all according to the present processes of synthesizing, respectively.

In some aspects the method of making the compound of formula (I) may be further defined by the nature of the composition of the reaction mixture in the optional substitution contacting step. The substitution contacting step may lack a vehicle; alternatively the substitution contacting step may further comprise a vehicle, wherein the compounds of formula (a1), (a2) and (b1), or the compounds (a3) and (b1), are in admixture with the vehicle during the substitution contacting step. The vehicle may be a hydrocarbon vehicle, wherein the compounds of formula (a1), (a2) and (b1), or the compounds (a3) and (b1), are in admixture with the hydrocarbon vehicle during the substitution contacting step. The hydrocarbon vehicle may function as a solvent for one or more of the compounds of formulas (a1), (a2), (a3), and/or (b1).

The hydrocarbon vehicle may consist of carbon and hydrogen atoms or a may be halogenated hydrocarbon vehicle consisting of carbon, hydrogen, and halogen atoms. The hydrocarbon vehicle consisting of C and H atoms may be alkanes, aromatic hydrocarbons, and mixtures of any two or more thereof. The alkanes may be hexanes, cyclohexane, heptanes, isoparaffins, or mixtures of any two or more thereof. The aromatic hydrocarbon may be toluene, xylenes, or mixtures of any two or more thereof. The halogenated hydrocarbon vehicle may be dichloromethane. The hydrocarbon vehicle may remain in the reaction mixture when the reduction contacting step is performed; alternatively the hydrocarbon vehicle may be removed from the reaction mixture prior to performing the reduction contacting step. The methods having different compositions for hydrocarbon vehicle may differ from each other in at least one result, property, function, and/or use. Different hydrocarbon vehicles may provide different solubilities to the reactants and products, or different morphologies to solid salt by-products.

The contacting steps (e.g., the reduction contacting step and the optional substitution contacting step) independently may further comprise agitating the reactants (e.g., agitating the compound of formula (c1) and the aluminum hydride; and/or agitating the compounds of formulas (a1), (a2) and (b1), or the compounds (a3) and (b1); and agitating any additional ingredients (e.g., vehicle). The agitating may enhance mixing and contacting together of the reactants and additional ingredients in the reaction mixture.

Said contacting steps independently may use other conditions, with or without the agitating. The other conditions may be tailored to enhance the contacting, and thus reaction, of the reactants so as to form the intended reaction product in a particular contacting step. Said other conditions may be result effective conditions for enhancing reaction yield or minimizing amount of a particular reaction by-product. Examples of said other conditions are atmosphere, temperature, and pressure. For example, the reduction and/or substitution contacting steps independently may be performed under an inert gas atmosphere such as a bleed of anhydrous argon or helium gas. Alternatively or additionally, the reduction and/or substitution contacting steps independently may comprise a temperature of the reactants of from a minimum temperature at which said reaction can be appreciated, up to the lower of the boiling point of the lowest boiling ingredient at a pressure employed. Reaction may be appreciated by detecting disappearance of reactants or appearance of product, e.g., by $^{29}Si$ and/or $^1H$ nuclear magnetic resonance (NMR) spectroscopy. For example, the reduction and/or substitution contacting steps independently may comprise a temperature of the reactants of from −20° to 200° C., alternatively from 0° to 150° C., alternatively from 20° to 120° C., alternatively from 30° to 100° C. The reduction and/or substitution contacting steps independently may be performed under less than ambient pressure, e.g., less than 101.3 kilopascals, and therefore the aforementioned maximum temperatures may be lowered in relation to the lowering of the pressure. The conditions used in the different ones of the reduction and/or substitution contacting steps may be the same as or different than the conditions used in any other contacting step(s) and/or the separating steps described herein.

In some aspects of the method of making the compound of formula (I), if the reduction contacting step is carried out for too long prior to initiating the separating step, the yield of the purified compound of formula (I) from the separating step may be undesirably decreased. Therefore, it may be advantageous to perform the reduction contacting step and the separating step at the same time and under the same conditions. This co-performance of the reduction contacting and separating steps may be done, for example, by contacting the compound of formula (c1) and the aluminum hydride, and any optional additional ingredient (e.g., vehicle) together under conditions useful for both reducing the compound of formula (c1) to the compound of formula (I) and for separating the compound of formula (I) from the resulting reaction mixture such as via continuous distillation such as vacuum distillation, and soon after it is formed continuously separating the compound of formula (I) from the reaction mixture. In this way the yield of the purified compound of formula (I) may be optimized under the conditions employed because as soon as it is made, the compound of formula (I) is removed from the reaction mixture, and optionally cooled.

In some aspects the reaction mixture containing the compound of formula (I) is used directly as obtained from the reduction contacting step without purification. For example, the reaction mixture containing the compound of formula (I) may be stored until future use (e.g., in cold storage having temperature ≤−50° C.) or may be characterized directly for presence and amount of the compound of formula (I) therein. In other aspects the method of making the compound of formula (I) may be further defined by one or more optional subsequent steps that come after the reduction contacting step. The method may further comprise a subsequent step of separating the compound of formula (I) from the reaction by-product(s), or from any unreacted reactants, or from any additional reaction ingredient (e.g., vehicle), or from a combination of any two or more thereof, to give a purified compound of formula (I).

The separating step, when employed, may comprise any technique suitable for separating the compound of formula (I) from the reaction by-product and any unreacted reactants or additional ingredients (e.g., vehicle). Different techniques may be preferred for different compounds of formula (I). One technique may be employed or a sequence of two or more techniques may be employed. A given technique may be performed one time or repeated two or more times, each time with a product of a prior technique in order to iteratively decrease impurity content to yield an iteratively purified compound of formula (I), e.g., a purified compound of formula (I) having iteratively lower atomic concentrations of aluminum. Examples of suitable techniques are decanting, distilling, evaporating, extracting, filtering, freeze drying, gas chromatography, ion exchange chromatography, partitioning, phase separating, reverse phase liquid chromatography, stripping, volatilizing, and washing. Alternatively or additionally, the compound of formula (I) may be subjected to reverse phase liquid chromatography. Examples of suitable reverse phase liquid chromatography techniques are reverse phase medium pressure column chromatography (RP-MPLC) and reverse phase high pressure column chromatography (RP-HPLC), wherein the stationary phase is a solid such as silica gel and the mobile phase is an anhydrous, aprotic organic solvent such as anhydrous hexanes, anhydrous acetonitrile, anhydrous ethyl acetate, or a mixture of any two or more thereof.

For example, in some aspects the reduction contacting step may produce a reaction mixture having therein a solid carried over into the reduction contacting step (from a optional preliminary step), and/or having therein a solid precipitate formed in situ as a reaction by-product during the reduction contacting step. In said aspects the separating step may comprise filtering such a reaction mixture to remove the solids such as salts (e.g., MX such as LiCl, NaCl, NaBr, $MgCl_2$, as the case may be depending on X and M) to give a filtrate containing the compound of formula (I) and lacking solid reaction by-products.

The filtrate may be distilled or stripped to remove volatile components therefrom to give a remainder containing a concentrated form of the compound of formula (I). The volatile components removed in this way are components having a lower boiling point than the boiling point of the compound of formula (I) and may include, e.g., any unreacted amine(s) of formula $R^1R^2NH$ and/or $R^3R^4NH$; and/or any reaction by-products of Si—Si bond cleavage.

Any reaction by-products and other ingredients of a reaction mixture having a lower boiling point than the boiling point of the compound of formula (I) may be removed before removal of the compound of formula (I) via an evaporative method. The compound of formula (I) may be distilled or stripped from the remainder to give the purified compound of formula (I) and leave behind a pot residue comprising a remainder containing any non-volatile reaction by-products and/or any non-volatile additional ingredients. The non-volatile components left behind in this way are components having a higher boiling point than the boiling point of the compound of formula (I) and may include, e.g., non-volatile vehicle such as the alkylene glycol dialkyl ether vehicle and/or oligomeric or polymeric by-products formed by condensation of two or more silane molecules during the reduction contacting step.

The purity of the purified compound of formula (I) may be determined by reverse phase liquid chromatography or, more likely, by gas chromatography (GC) as described later. For example, the purity determined by GC may be from 60 area % to ≤100 area % (GC), alternatively from 70 area % to ≤100 area % (GC), alternatively from 80 area % to ≤100 area % (GC), alternatively from 90 area % to ≤100 area % (GC), alternatively from 93 area % to ≤100 area % (GC), alternatively from 95 area % to ≤100 area % (GC), alternatively from 97 area % to ≤100 area % (GC), alternatively from 99.0 area % to ≤100 area % (GC). Each ≤100 area % (GC) independently may be equal to 100 area % (GC), in which aspect the purified compound of formula (I) is the compound of formula (I) per se. Alternatively each ≤100 area % (GC) independently may be <100 area % (GC), in which aspect the purified compound of formula (I) is the composition. The maximum purity of the composition having <100 area % (GC) may be 99.9999999 area % (GC) ("nine 9's" purity), alternatively 99.999999 area % (GC) ("eight 9's" purity), alternatively 99.99999 area % (GC) ("seven 9's" purity), alternatively 99.9999 area % (GC) ("six 9's" purity), alternatively 99.999 area % (GC) ("five 9's" purity), alternatively 99.99 area % (GC) ("four 9's" purity), alternatively 99.9 area % (GC), all of the compound of formula (I). It is believed that the compound of formula (I), or the composition that consists essentially of the foregoing six 9's to nine 9's purity of the compound of formula (I), may be particularly useful in making silicon materials for electronics and/or photovoltaic applications, wherein generally the higher the number of 9's purity the better the usefulness thereof in said applications.

Another aspect of the invention is the method of making a compound of formula (I):

$(R^1R^2N)Si_nH_{2n}(NR^3R^4)$ (I)

wherein subscript n is 3-9; $R^1$ is methyl, propyl, butyl, pentyl, hexyl, $(C_3-C_6)$cycloalkyl, $(C_2-C_6)$alkenyl, $(C_2-C_6)$alkynyl, or phenyl, and each $R^2$, $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ is H and each of $R^2$, $R^3$, and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^3$ are H and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be $—R^{1a}—R^{2a}—$ wherein $—R^{1a}—R^{2a}—$ is $(C_2-C_5)$alkylene and each $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be $—R^{1a}—R^{2a}—$ wherein $—R^{1a}—R^{2a}—$ is $(C_2-C_5)$alkylene and $R^3$ and $R^4$ are bonded together to be $—R^{3a}—R^{4a}—$ wherein $—R^{3a}—R^{4a}—$ is $(C_2-C_5)$alkylene; or $R^1$ and $R^3$ are bonded together to be $—R^{1a}—R^{3a}—$ wherein $—R^{1a}—R^{3a}—$ is $(C_2-C_5)$alkylene and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; and the $R^1R^2N—$ and $—NR^3R^4$ groups are bonded to a same silicon atom or to different silicon atom in the compound of formula (I), the method comprising: contacting a compound of formula (d1): $(R^1R^2N)Si_nH_{2n+1}$ (d1) with a compound of formula (d2) $(NR^3R^4)$ (d2), wherein n, $R^1$, $R^2$, $R^3$, and $R^4$ are as defined above, in the presence of a catalyst, wherein the catalyst comprises at least one of the main group elements Li, Na, K, Rb, Cs, Be, Mg, Ca, Sr, Ba, B, Al, Ga, In, Tl, C, Si, Ge, Sn, Pb, N, P, As, Bb, Bi, O, S, Se, Te, F, Cl, Br, I, Zn, Cd or Hg to give a reaction mixture; maintaining the reaction mixture at a temperature between about 0° C. to about 250° C.; allowing the reaction to proceed to form the compound of formula (I) above; separating the compound of formula (I) of the compound of formula (I) from the reaction mixture; wherein the reaction mixture temperature may vary during the synthesis and is maintained such that the temperature of the reaction mixture is not allowed to drop below about 0° C. and not exceed about 250° C.

Another aspect of the invention is the method of making a silicon-containing material, the method comprising subjecting a source gas comprising the compound of formula (I) to silicon deposition conditions in the presence of a substrate, to give a silicon-containing material formed on the substrate. In the method the compound of formula (I) functions as a silicon-yielding precursor. The substrate may be composed of any material suitable for supporting another material (e.g., film). The material may be homogeneous or heterogeneous (e.g., a composite material or structure). The substrate or a surface thereof may be continuous or discontinuous.

In some aspects the method of making the silicon-containing material produces same in a form of a film, rod, or particles. Results obtained from the method may be further influenced by defining the composition of the source gas. The source gas may contain only the compound of formula (I). The compound of formula (I) may be used as a source of silicon only in the silicon-containing material. The silicon-containing material so formed may be an elemental silicon, e.g., an amorphous or crystalline silicon. The crystalline silicon may be monocrystalline silicon, alternatively polycrystalline silicon. Alternatively, the compound of formula (I) may be used as a source of silicon and carbon; silicon and nitrogen; or silicon, carbon and nitrogen. The methods having different compositions for the composition of formula (I) may differ from each other in at least one result, property, function, and/or use. When the compound of formula (I) is used as the only silicon yielding precursor, the film-forming process is significantly simplified.

Alternatively the source gas may contain a combination of the compound of formula (I) and at least one other source gas. The combination of any two or more of the additional precursors is chosen to provide the ad rem material (e.g., SiC, or SiN) with the intended non-Si element(s) (e.g., C, N, and/or O). Said combination may be useful when the intended silicon-containing material contains oxygen, which the compound of formula (I) lacks, or when it is desirable for the intended silicon-containing material to contain a higher concentration of carbon and/or nitrogen than can be supplied from the compound of formula (I) alone under the deposition conditions employed.

The at least one other source gas may contain silicon, alternatively may lack silicon. The at least one other source gas may contain an additional precursor that functions as a source of carbon, alternatively nitrogen, alternatively oxygen, alternatively carbon and nitrogen, alternatively oxygen and nitrogen. The additional precursor may be a source of carbon comprising a carbon-containing precursor, a source of oxygen comprising an oxygen-containing precursor (e.g., molecular oxygen, ozone, nitrous oxide, water, or hydrogen peroxide), or a source of nitrogen comprising nitrogen-containing precursor (e.g., anhydrous ammonia, molecular nitrogen, or hydrazine), or a combination of any two or more of the source of carbon comprising a carbon-containing precursor, the source of oxygen comprising an oxygen-containing precursor, and the source of nitrogen comprising nitrogen-containing precursor.

In some aspects, the method of making the silicon-containing material (e.g., film) may be further defined by the chemical composition of the silicon-containing material it produces. The silicon-containing material may comprise elemental silicon (e.g., an amorphous, monocrystalline, or polycrystalline silicon), silicon carbide, silicon nitride, silicon oxide, silicon oxynitride, or silicon-carbo-nitride. Alternatively, the silicon-containing material may comprise elemental silicon; alternatively a silicon carbide, silicon nitride, silicon oxide, silicon oxynitride, or silicon-carbo-nitride; alternatively a silicon carbide, silicon nitride, or silicon-carbo-nitride; alternatively a silicon oxide or silicon oxynitride; alternatively silicon carbide, alternatively silicon nitride, alternatively silicon oxide, alternatively silicon oxynitride, alternatively silicon-carbo-nitride. The elemental silicon material (e.g., film) consists essentially of Si atoms and may be amorphous, polycrystalline, or epitaxial. In some aspects the silicon-containing material may be further defined by its electrical character. For example, the silicon-containing material may be a semiconductor material such as the elemental silicon or silicon carbide. Alternatively the silicon-containing material may be a dielectric material such as silicon nitride, silicon oxide, silicon oxynitride, or silicon-carbonitride.

The elemental silicon may be prepared from the compound of formula (I) alone or from a precursor combination comprising the compound of formula (I) and a perhydridosilane (e.g., $SiH_4$ or $Si_2H_6$). The silicon carbide material may be prepared from the compound of formula (I) alone or from a precursor combination comprising the compound of formula (I) and a mixture of the carbon-containing precursor lacking N and O. The carbon-containing precursor lacking N and O and useful for preparing the silicon carbide material may be trimethyl- or tetramethyl-monosilane, dichlorodimethyl-monosilane, or chlorotrimethyl-monosilane, or a silaalkane such as 1,3-disilabutane. The silicon carbonitride material may be prepared from the compound of formula (I) alone or from a precursor combination comprising the compound of formula (I) and a mixture of the carbon-containing and nitrogen-containing precursor(s), which is a collection of molecules containing both C and N and lacking O or are different molecules in that one additional precursor contains C but not N or O and the other additional precursor contains N but not C or O. The carbon-and-nitrogen-containing precursor useful for preparing the silicon carbonitride material may be alkylaminosilane such as tris(dimethylamino)silane and the carbon-containing and nitrogen-containing precursors may be a mixture of different molecules such as a mixture of trimethyl or tetramethyl-monosilane and ammonia. Alternatively, the silicon carbonitride material may be prepared from a precursor combination comprising the compound of formula (I) and a carbon-and-nitrogen-containing precursor or a collection of such precursors wherein each such precursor contains C and N. The silicon oxycarbonitride material may be prepared from the compound of formula (I) alone or from a precursor combination comprising the compound of formula (I) and (a) a mixture the carbon-containing precursor and an oxygen-containing precursor such as molecular oxygen or (b) a carbon-and-oxygen-containing precursor such as an organosiloxane such as hexamethyldisiloxane or a cyclic organosiloxane such as tetrakis(dimethylsiloxane) (commonly referred to as "D4").

In some aspects the method of making the silicon-containing material (e.g., film) may be further defined by the silicon deposition method. The material (e.g., film) deposition method may be a chemical vapor deposition (CVD) method; alternatively an atomic layer deposition (ALD or ALCVD) method; alternatively a plasma enhanced chemical vapor deposition method or a thermal chemical vapor deposition method. Examples of suitable vapor deposition methods are CVD and ALD. The CVD methods may be categorized broadly as thermal or heat based or plasma enhanced (PE). Examples of types of CVD methods that are useful include APCVD (atmospheric pressure (AP) 95 to 105 kilopascals), LPCVD (low pressure (LP) 0.001 pascals (Pa.) <pressure <10 Pa.), UHVCVD (ultrahigh vacuum (UHV) pressure <1×10$^{-6}$ pascals), PECVD, ALCVD, CCVD (thermal based), HWCVD (thermal based), HPCVD, RTCVD (thermal based), VPE (thermal based), and PICVD. Solution deposition involves polymerization of a volatile precursor from solution onto a substrate or deposition of a nonvolatile polymer from solution onto a substrate. Examples of suitable solution deposition methods are spray coating, dip coating, printing, and SOD. The solution deposition method may be spray coating or SOD, alternatively spray coating, alternatively dip coating, alternatively printing, alternatively SOD.

Another aspect of the invention is the use of the compound of formula (I) in the making of a silicon-containing material comprising elemental silicon, silicon carbide, silicon nitride, silicon oxide, silicon oxynitride, or silicon-carbo-nitride. In some aspects the silicon-containing material is a film, alternatively a rod, alternatively particles.

Another aspect of the invention is the compound of formula (c1): $(R^1R^2N)Si_nX_{2n}(NR^3R^4)$ (c1), wherein subscript n is an integer from 3 to 9; each X independently is a halogen atom selected from Cl, Br, and I; $R^1$ is methyl, propyl, butyl, pentyl, hexyl, $(C_3$-$C_6)$cycloalkyl, $(C_2$-$C_6)$alkenyl, $(C_2$-$C_6)$alkynyl, or phenyl, each $R^2$, $R^3$ and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl; or $R^1$ is H and each of $R^2$, $R^3$, and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl; or $R^1$ and $R^3$ are H and each of $R^2$ and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl; or $R^1$ and $R^2$ are bonded together to be —$R^{1a}$—$R^{2a}$— wherein —$R^{1a}$—$R^{2a}$— is $(C_2$-$C_5)$alkylene and each $R^3$ and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl; or $R^1$ and $R^2$ are bonded together to be —$R^{1a}$—$R^{2a}$— wherein —$R^{1a}$—$R^{2a}$— is $(C_2$-$C_5)$alkylene and $R^3$ and $R^4$ are bonded together to be —$R^{3a}$—$R^{4a}$— wherein —$R^{3a}$—$R^{4a}$— is $(C_2$-$C_5)$alkylene; or $R^1$ and $R^3$ are bonded together to be —$R^{1a}$—$R^{3a}$— wherein —$R^{1a}$—$R^{3a}$— is $(C_2$-$C_5)$alkylene and each of $R^2$ and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl; and the $R^1R^2N$— and —$NR^3R^4$ groups are bonded to a same silicon atom or to different silicon atoms in the compound of formula (c1). In some aspects of the compound of formula (c1) each $R^1$, $R^2$, $R^3$ and $R^4$ independently is defined as described in any one of the above aspects of the compound of formula (I). In some aspects of the compound of formula (c1) each X is as defined in any one of the above aspects for the method of making the compound of formula (I). In some aspects of the compound of formula (c1), X is Cl and n, $R^1$, $R^2$, $R^3$ and $R^4$ are as described in any one of the above aspects for the compound of formula (I). The compounds of formula (c1) having different compositions for the X, n, $R^1$, $R^2$, $R^3$ and/or $R^4$ may differ from each other in at least one property, function, and/or use.

In some aspects the compound of formula (c1) is 1,1-bis(diisopropylamino)hexachlorotrisilane; 1,2-bis(diisopropylamino)hexachlorotrisilane; 1,3-bis(diisopropylamino)hexachlorotrisilane; 2,2-bis(diisopropylamino)hexachlorotrisilane; 1,2-bis(diisopropylamino)octachlorotetrasilane; 1,3-bis(diisopropylamino)octachlorotetrasilane; 1,4-bis(diisopropylaminodiisopropylamino)octachlorotetrasilane; 1,5-bis(diisopropylamino)decachloropentasilane; 1,3-bis(diisopropylamino)-decachloro-2,2-bissilyltrisilane; or 1,1-bis(diisopropylamino)-decachloro-2,2-bissilyltrisilane. Alternatively, any one of the foregoing species may be omitted and the compound of formula (c1) may be selected from the group consisting of any of the remaining nine species. In the method of synthesizing the compound of formula (I), any one of the foregoing species yields the corresponding 1,1-bis(diisopropylamino)trisilane; 1,2-bis(diisopropylamino)trisilane; 1,3-bis(diisopropylamino)trisilane; 2,2-bis(diisopropylamino)trisilane; 1,2-bis(diisopropylamino)tetrasilane; 1,3-bis(diisopropylamino)tetrasilane; 1,4-bis(diisopropylaminodiisopropylamino)tetrasilane; 1,5-bis(diisopropylamino)pentasilane; 1,3-bis(diisopropylamino)-2,2-bissilyltrisilane; or 1,1-bis(diisopropylamino)-2,2-bissilyltrisilane, respectively.

In some aspects the compound of formula (c1) is 1,1-bis(diisopropylamino)hexabromotrisilane; 1,2-bis(diisopropylamino)hexabromotrisilane; 1,3-bis(diisopropylamino)hexabromotrisilane; 2,2-bis(diisopropylamino)hexabromotrisilane; 1,2-bis(diisopropylamino)octabromotetrasilane; 1,3-bis(diisopropylamino)octabromotetrasilane; 1,4-bis(diisopropylamino)octabromotetrasilane; 1,5-bis(diisopropylamino)decabromopentasilane; 1,3-bis(diisopropylamino)-decabromo-2,2-bissilyltrisilane; or 1,1-bis (diisopropylamino)-decabromo-2,2-bissilyltrisilane. Alternatively, any one of the foregoing species may be omitted and the compound of formula (c1) may be selected from the group consisting of any of the remaining nine species. In the method of synthesizing the compound of formula (I), any one of the foregoing species yields the corresponding 1,1-bis(diisopropylamino)trisilane; 1,2-bis(diisopropylamino)trisilane; 1,3-bis(diisopropylamino)trisilane; 2,2-bis(diisopropylamino)trisilane; 1,2-bis(diisopropylamino)tetrasilane; 1,3-bis(diisopropylamino)tetrasilane; 1,4-bis(diisopropylamino)tetrasilane; 1,5-bis(diisopropylamino)pentasilane; 1,3-bis(diisopropylamino)-2,2-bissilyltrisilane; or 1,1-bis(diisopropylamino)-2,2-bissilyltrisilane, respectively.

Another aspect of the invention is a composition comprising the compound of formula (c1) and at least one additional ingredient that is not a compound of formula (c1) or (I). The composition may comprise 1,3-bis(diisopropylamino)hexachlorotrisilane and at least one additional ingredient that is not a compound of formula (c1) or (I).

In some aspects of the compound of formulas (c1) and (I), each of $R^1$ and $R^2$ independently is $(C_1$-$C_6)$alkyl, $(C_3$-$C_6)$cycloalkyl, $(C_2$-$C_6)$alkenyl, $(C_2$-$C_6)$alkynyl, or phenyl. In some aspects of the compound of formulas (c1) and (I), $R^1$ is H and $R^2$, $R^3$ and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl. In some aspects $R^1$ and $R^2$ is H and each of $R^2$ and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl. In some aspects of the compound of formulas (c1) and (I), $R^1$ and $R^2$ are bonded together to be —$R^{1a}$—$R^{2a}$— wherein —$R^{1a}$—$R^{2a}$— is $(C_2$-$C_5)$alkylene. In some aspects of the compound of formulas (c1) and (I), each of $R^3$ and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl. In some aspects of the compound of formulas (c1) and (I), $R^3$ is H and $R^4$ is $(C_1$-$C_6)$alkyl, $(C_3$-$C_6)$cycloalkyl, $(C_2$-$C_6)$alkenyl, $(C_2$-$C_6)$alkynyl, or phenyl. In some aspects of the compound of formulas (c1) and (I), $R^3$ and $R^4$ are bonded together to be —$R^{3a}$—$R^{4a}$— wherein —$R^{3a}$—$R^{4a}$— is $(C_2$-$C_5)$alkylene.

Another aspect of the invention is the method of making the compound of formula (c1), the method comprising: contacting one molar equivalent of a compound of formula (a1): $R^1R^2NM$ (a1) and one molar equivalent of a compound of formula (a2): $R^3R^4NM$ (a2), or contacting one molar equivalent of a compound of formula (a3) $M(R^2)N$—$R^{1a}$—$R^{3a}$—$N(R^4)M$ (a3), with a compound of formula (b1): $Si_nX_{2n+2}$ (b1) to give a compound of formula (c1): $(R^1R^2N)Si_nX_{2n}(NR^3R^4)$ (c1), wherein each M independently is a Group I element selected from H, Li, Na, and K; each X independently is a halogen atom selected from Cl, Br, and I; and n, $R^1$, $R^2$, $R^3$, and $R^4$ are as defined immediately in any one of the above aspects; and the $R^1R^2N$— and —$NR^3R^4$ groups are bonded to a same silicon atom or to different silicon atoms in the compound of formula (c1). In some aspects the method comprises the contacting one molar equivalent of a compound of formula (a1): $R^1R^2NM$ (a1) and one molar equivalent of a compound of formula (a2): $R^3R^4NM$ (a2), with a compound of formula (b1): $Si_nX_{2n+2}$ (b1) to give a compound of formula (c1). In other aspects the method comprises contacting one molar equivalent of a compound of formula (a3) $M(R^2)N$—$R^{1a}$—$R^{3a}$—$N(R^4)M$ (a3) with a compound of formula (b1): $Si_nX_{2n+2}$ (b1) to give a compound of formula (c1). In still other aspects the method comprises contacting a molar equivalent, p, of a compound of formula (a1): $R^1R^2NM$ (a1), and a molar equivalent, p, of a compound of formula (a2): $R^3R^4NM$ (a2), and a molar equivalent, q, of a compound of formula (a3) $M(R^2)N$—$R^{1a}$—$R^{3a}$—$N(R^4)M$ (a3), with a molar equivalent, r, of a compound of formula (b1): $Si_nX_{2n+2}$ (b1) to give the compound of formula (c1), wherein each of p and q is >0 and wherein q+(p/2)=r. The methods having different compositions for the compounds of formulas (a1), (a2) and (b1), or (a3) and (b1) may differ from each other, and differ from the compound of formula (c1), in at least one result, property, function, and/or use.

In some aspects the reaction mixture containing the compound of formula (c1) is used directly as obtained from the substitution contacting step without purification. For example, the reaction mixture containing the compound of formula (c1) may be stored until future use (e.g., in cold storage having temperature ≤−50° C.) or may be characterized directly for presence and amount of the compound of formula (c1) therein, or may be used directly in the reduction contacting step. In other aspects the method of making the compound of formula (c1) may be further defined by one or more optional subsequent steps that come after the substitution contacting step.

The method of making the compound of formula (c1) may further comprise a subsequent step of separating the compound of formula (c1) from the reaction by-product(s), or from any unreacted reactants, or from any additional reaction ingredient (e.g., vehicle), or from a combination of any two or more thereof, to give a purified compound of formula (c1). The methods of separating the compound of formula (c1) from the reaction mixture formed in this substitution contacting step may be analogous to, and readily adapted from, the aforementioned methods of separating the compound of formula (I) from the reaction mixture formed in the reduction contacting step, except wherein the compound of formula (c1) is expected to have a boiling point that is higher than the boiling point of the corresponding compound of formula (I).

In some aspects of the method of making the compound of formula (c1), if the substitution contacting step is carried out for too long prior to initiating the optional separating step, the yield of the purified compound of formula (c1) from the separating step may be undesirably decreased. Therefore, it may be advantageous to perform the substitution contacting step and the separating step at the same time and under the same conditions. This co-performance of the substitution contacting and separating steps may be done, for example, by contacting the compounds of formulas (a1), (a2) and (b1), or by contacting the compounds of formulas (a3) and (b1), and any optional additional ingredient (e.g., vehicle) together under conditions useful for both condensing together the compounds of formulas (a1), (a2) and (b1), or (a3) and (b1), to give the compound of formula (c1) and for separating the compound of formula (c1) from the resulting reaction mixture such as via continuous distillation such as vacuum distillation, and soon after it is formed continuously separating the compound of formula (c1) from the reaction mixture. In this way the yield of the purified compound of formula (c1) may be optimized under the conditions employed because as soon as some of it is made, the compound of formula (c1) is removed from the reaction mixture, and optionally cooled.

The purity of the purified compound of formula (c1) may be determined by $^{29}$Si—NMR, reverse phase liquid chromatography or, more likely, by gas chromatography (GC) as described later. For example, the purity determined by GC may be from 60 area % to ≤100 area % (GC), alternatively from 70 area % to ≤100 area % (GC), alternatively from 80 area % to ≤100 area % (GC), alternatively from 90 area % to ≤100 area % (GC), alternatively from 93 area % to ≤100 area % (GC), alternatively from 95 area % to ≤100 area % (GC), alternatively from 97 area % to ≤100 area % (GC), alternatively from 99.0 area % to ≤100 area % (GC). Each ≤100 area % (GC) independently may be as defined previously.

Compositions having different purities of the compound of formula (c1) may differ from each other in at least one result, property, function, and/or use. It is believed that the compound of formula (c1), or a composition that consists essentially of six 9's to nine 9's purity of the compound of formula (c1), may be particularly useful as an intermediate for making silicon-yielding precursors for producing silicon materials for electronics and/or photovoltaic applications, wherein generally the higher the number of 9's purity the better the usefulness thereof in said applications.

Another aspect of the invention is the use of the compound of formula (c1) in the synthesis of the compound of formula (I).

Another aspect of the invention is the method of a method of making a compound of formula (I): $(R^1R^2N)Si_nH_{2n}(NR^3R^4)$ (I), wherein subscript n is an integer from 3 to 9; $R^1$ is methyl, propyl, butyl, pentyl, hexyl, $(C_3$-$C_6)$cycloalkyl, $(C_2$-$C_6)$alkenyl, $(C_2$-$C_6)$alkynyl, or phenyl, and each $R^2$, $R^3$ and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl; or $R^1$ is H and each of $R^2$, $R^3$, and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl; or $R^1$ and $R^3$ are H and each of $R^2$ and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl; or $R^1$ and $R^2$ are bonded together to be —$R^{1a}$—$R^{2a}$— wherein —$R^{1a}$—$R^{2a}$— is $(C_2$-$C_5)$alkylene and each $R^3$ and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl; or $R^1$ and $R^2$ are bonded together to be —$R^{1a}$—$R^{2a}$— wherein —$R^{1a}$—$R^{2a}$— is $(C_2$-$C_5)$alkylene and $R^3$ and $R^4$ are bonded together to be —$R^{3a}$—$R^{4a}$— wherein —$R^{3a}$—$R^{4a}$— is $(C_2$-$C_5)$alkylene; or $R^1$ and $R^3$ are bonded together to be —$R^{1a}$—$R^{3a}$— wherein —$R^{1a}$—$R^{3a}$— is $(C_2$-$C_5)$alkylene and each of $R^2$ and $R^4$ independently is $(C_1$-$C_6)$alkyl, $(C_3$-$C_6)$cycloalkyl, $(C_2$-$C_6)$alkenyl, $(C_2$-$C_6)$alkynyl, or phenyl; and the $R^1R^2N$— and —$NR^3R^4$ groups are bonded to a same silicon atom or to different silicon atom in the compound of formula (I), the method comprising:

contacting a compound of formula (d1): $(R^1R^2N)Si_nH_{2n+1}$ (d1) with a compound of formula (d2) $(HNR^3R^4)$ (d2), wherein n, $R^1$, $R^2$, $R^3$, and $R^4$ are as defined above, in the presence of a catalyst, wherein the catalyst comprises at least one of the main elements Li, Na, K, Rb, Cs, Be, Mg, Ca, Sr, Ba, B, Al, Ga, In, Tl, C, Si, Ge, Sn, Pb, N, P, As, Bb, Bi, O, S, Se, Te, F, Cl, Br, I, Zn, Cd, or Hg to give a reaction mixture;

maintaining the reaction mixture ast a temperature between about 0° C. to about 250° C.; allowing the reaction to proceed to form the compound of formula (I) above;

separating the compound of formula (I) of the compound of formula (I) from the reaction mixture;

wherein the reaction mixture temperature may vary during the synthesis and is maintained such that the temperature of the reaction mixture is not allowed to drop below about 0° C. and not exceed about 250° C.

The catalyst comprises at least one of the elements Li, Na, K, Rb, Cs, Be, Mg, Ca, Sr, Ba, B, Al, Ga, In, Tl, C, Si, Ge, Sn, Pb, N, P, As, Bb, Bi, O, S, Se, Te, F, Cl, Br, I, Zn, Cd, or Hg alternatively Mg, Ca, Sr, Ba, B, Al, Ga, Ge or Sn.

The catalysts may be a homogeneous or heterogeneous catalyst, may be supported or unsupported, and may be a composite catalyst. A homogeneous catalyst forms a solution with the reactants and any solvent. A heterogeneous catalyst is not soluble in the reactants and/or any solvent present in the reaction.

Catalyst supports can be any typical support, alternatively the support is carbon or an oxide such as silicon dioxide or alumina.

The compound according to formula (d1) may be made by contacting a compound of formula $R^1R^2NH$ with a compound of formula $Si_nH_{2(n+1)}$, wherein n, $R^1$ and $R^2$ are as defined above, in the presence of a catalyst, wherein the catalyst comprises at least one of the main group elements Li, Na, K, Rb, Cs, Be, Mg, Ca, Sr, Ba, B, Al, Ga, In, Tl, C, Si, Ge, Sn, Pb, N, P, As, Bb, Bi, O, S, Se, Te, F, Cl, Br, I, Zn, Cd or Hg to give a reaction mixture; maintaining the reaction mixture at a temperature between about 0° C. to about 250° C.; allowing the reaction to proceed to form the compound of formula (d1) above; separating the compound of formula (d1) from the reaction mixture; wherein the reaction mixture temperature may vary during the synthesis and is maintained such that the temperature of the reaction mixture is not allowed to drop below about 0° C. and not exceed about 250° C.

The compound of formula (I) may be separated from the other reactants by, for example, distillation.

The reaction temperature is from 0 to 250° C., alternatively from 0 to 60° C., alternatively from 15 to 45° C.

The method can be carried out in typical reactors for such reactions. Once skilled in the art would know how to select a reactor to perform the method of the invention.

The invention is further illustrated by, and an invention embodiment may include any combinations of features and limitations of, the non-limiting examples thereof that follow. Ambient temperature is about 23° C. unless indicated otherwise.

Gas Chromatography-Flame Ionization Detector (GC-FID) conditions: a capillary column with 30 meters length, 0.32 mm inner diameter, and containing a 0.25 μm thick stationary phase in the form of a coating on the inner surface of the capillary column, wherein the stationary phase was composed of phenyl methyl siloxane. Carrier gas was helium gas used at a flow rate of 105 mm per minute. GC instrument was an Agilent model 7890A gas chromatograph. Inlet temperature was 150° C. GC experiment temperature profile consisted of soaking (holding) at 50° C. for 2 minutes, ramping temperature up at a rate of 15° C./minute to 250° C., and then soaking (holding) at 250° C. for 10 minutes.

GC-MS instrument and conditions: Sample was analyzed by electron impact ionization and chemical ionization gas chromatography-mass spectrometry (EI GC-MS and Cl GC-MS). Agilent 6890 GC conditions included a DB-1 column with 30 meters (m)×0.25 millimeter (mm)×0.50 micrometer (μm) film configuration. An oven program of soaking at 50° C. for 2 minutes, ramping at 15° C./minute to 250° C., and soaking at 250° C. for 10 minutes. Helium carrier gas flowing at constant flow of at 1 mL/minute and a 50:1 split injection. Agilent 5973 MSD conditions included a MS scan range from 15 to 800 Daltons, an EI ionization and Cl ionization using a custom Cl gas mix of 5% $NH_3$ and 95% $CH_4$.

$^{29}$Si-NMR instrument and solvent: a Varian 400 MHz Mercury spectrometer was used. $C_6D_6$ was used as the solvent.

$^1$H-NMR instrument and solvent: a Varian 400 MHz Mercury spectrometer was used. $C_6D_6$ was used as the solvent.

EXAMPLE (EX.) 1 (PROPHETIC)

Synthesis of 1,3-bis(diisopropylamino)hexachlorotrisilane (i-Pr$_2$NSiCl$_2$SiCl$_2$SiCl$_2$N(i-Pr)$_2$): Add diisopropylamine (i-Pr$_2$NH; 9.28 mL, 66.4 mmol) to a 0.82 M solution of n-butyl lithium (n-BuLi; 66.4 mmol) in hexanes and maintained temperature ≤40° C. After the addition, agitate the resultant lithium diisopropylamide (LDA) solution for 1 hour. Then add the LDA solution to a solution of octachlorotrisilane (Si$_3$Cl$_8$; 11.1 g, 30.1 mmol) in hexanes (20 mL) at temperature about −15° C. A pale-white slurry forms. After warming to room temperature, filter the slurry to remove salt by-products. Vacuum strip the resulting clear filtrate to remove volatile components, leaving a liquid remainder. Analyze the composition of the remainder by $^{29}$Si-NMR to find i-Pr$_2$NSiCl$_2$SiCl$_2$SiCl$_2$N(i-Pr)$_2$.

EX. 2 (PROPHETIC)

Synthesis of 1,3-bis(diisopropylamino)trisilane (i-Pr$_2$NSiH$_2$SiH$_2$SiH$_2$N(i-Pr)$_2$): Slurry LiAlH$_4$ (0.524 g, 13.8 mmol) in monoglyme (12.4 mL). Add the remainder of Ex. 1 (4.1 g; approximately 50.0 mmol SiCl group) to the slurry at about −18° C. to form a slurry. After warming the resulting slurry up to room temperature (24° C.), filter the reaction mixture to remove insoluble salt by-products. Vacuum distill the filtrate with a simple vacuum distillation apparatus to remove monoglyme first, and then to give a liquid condensed in a receiver cooled with dry ice. The liquid contains 1,3-bis(diisopropylamino)trisilane (i-Pr$_2$NSiH$_2$SiH$_2$SiH$_2$N(i-Pr)$_2$) based on gas chromatography-flame ionization detector (GC-FID) integration results. Also characterize the liquid by gas chromatograph-mass spectrometry (GC-MS) and $^1$H-NMR.

EX. 3 (PROPHETIC)

Synthesis of 1,3-bis(diisopropylamino)trisilane (i-Pr$_2$NSiH$_2$SiH$_2$SiH$_2$N(i-Pr)$_2$): Slurry LiAlH$_4$ (0.524 g, 13.8 mmol) in monoglyme (12.4 mL). Add the remainder of Ex. 1 (4.1 g; approximately 50.0 mmol SiCl group) to the slurry at about −18° C. to form a slurry. After warming the resulting slurry up to room temperature (24° C.), add a high boiling point solvent (alkane) that boils at a temperature higher than the boiling point of 1,3-bis(diisopropylamino)trisilane. Then vacuum distill the mixture with a simple vacuum distillation apparatus to remove monoglyme first, and then to give a liquid condensed in a receiver cooled with dry ice. The liquid contains 1,3-bis(diisopropylamino)trisilane (i-Pr$_2$NSiH$_2$SiH$_2$SiH$_2$N(i-Pr)$_2$) based on GC-FID integration results. Also characterize the liquid by GC-MS and $^1$H-NMR.

As shown in the Ex. 1, 2 and 3, the compound of formula (I) would be synthesized according to the method of making same, purified, and characterized.

EX. 4 (PROPHETIC)

The liquid of Ex. 2 or 3 is subjected to fractional distillation under vacuum to give a distillate containing 1,3-bis(diisopropylamino)trisilane having a purity of at least 90 area % (GC).

EX. 5 (PROPHETIC)

Forming a silicon nitride film using the 1,3-bis(diisopropylamino)trisilane of Ex. 4 as a single-source Si-yielding precursor with LPCVD: using a LPCVD reactor and a bubbler containing the 1,3-bis(diisopropylamino)trisilane of Ex. 4 and in fluid communication with the LPCVD reactor, heat the bubbler containing 1,3-bis(diisopropylamino)trisilane to 70° C. to increase vapor pressure thereof. Then flow He carrier gas through the bubbler to carry vapor of 1,3-bis(diisopropylamino)trisilane into the LPCVD reactor, wherein the LPCVD reactor contains a plurality of vertically oriented and spaced apart silicon wafers heated to 500° C. so a conformal silicon nitride film is formed on the wafers.

EX. 6 (PROPHETIC)

Forming a silicon nitride film using the 1,3-bis(diisopropylamino)trisilane of Ex. 4 and ammonia (NH$_3$) with LPCVD: using a LPCVD reactor and a bubbler containing the 1,3-bis(diisopropylamino)trisilane of Ex. 4 and in fluid communication with the LPCVD reactor. Feed ammonia diluted in helium to the LPCVD reactor. Heat the bubbler containing 1,3-bis(diisopropylamino)trisilane to 70° C. to increase vapor pressure thereof. Then flow He carrier gas through the bubbler to carry vapor of 1,3-bis(diisopropylamino)trisilane into the LPCVD reactor, wherein the LPCVD reactor contains vaporous ammonia and a plurality of vertically oriented and spaced apart silicon wafers heated to 500° C. so a conformal silicon nitride film is formed on the wafers. The silicon nitride film formed in this way contains less carbon than the silicon nitride film formed in Ex. 5.

EX. 7 (PROPHETIC)

Forming a silicon nitride film using the 11,3-bis(diisopropylamino)trisilane of Ex. 4 with PECVD: using a PECVD reactor and a bubbler in fluid communication with the PECVD reactor, heat the bubbler containing the 1,3-bis(diisopropylamino)trisilane to 70° C. to increase vapor pressure thereof. Then flow He carrier gas through the bubbler to carry vapor of the 1,3-bis(diisopropylamino)trisilane into the PECVD reactor, wherein the PECVD reactor has an ammonia-derived plasma and contains a plurality of horizontally oriented and spaced apart silicon wafers heated to 500° C. such that a conformal silicon nitride film is formed on the wafers.

EX. 8 (PROPHETIC)

Forming a silicon oxide film using the 1,3-bis(diisopropylamino)trisilane of Ex. 4 with LPCVD: using a LPCVD reactor and a bubbler in fluid communication with the LPCVD reactor, heat the bubbler containing the 1,3-bis(diisopropylamino)trisilane to 70° C. to increase vapor pressure thereof. Then flow He carrier gas through the bubbler to carry vapor of the 1,3-bis(diisopropylamino)trisilane into the LPCVD reactor, wherein the LPCVD reactor has an oxygen atmosphere and contains a plurality of vertically oriented and spaced apart silicon wafers heated to 500° C. such that a conformal silicon oxide film is formed on the wafers.

EX. 9 (PROPHETIC)

Forming a silicon oxide film using the 1,3-bis(diisopropylamino)trisilane of Ex. 4 with spray coating: apply a 5 wt % solution of 1,3-bis(diisopropylamino)trisilane in toluene to a silicate glass dish (substrate) in air, allowed the toluene to evaporate so as to form a liquid coating of 1,3-bis (diisopropylamino)trisilane on the dish, and allowed the 1,3-bis(diisopropylamino)trisilane to air oxidize over 30 minutes at 25° C. such that a conformal silicon oxide film was formed on the dish.

EX. 10 (PROPHETIC)

Forming a silicon film using 1,3-bis(diisopropylamino)trisilane of Ex. 4 with LPCVD: use a LPCVD reactor, a bubbler containing the 1,3-bis(diisopropylamino)trisilane, and a bubbler containing disilane ($Si_2H_6$), wherein each bubbler is independently in fluid communication with the LPCVD reactor. Heat the bubbler containing 1,3-bis(diisopropylamino)trisilane to 70° C. to increase vapor pressure thereof. Then flow He carrier gas through the bubbler to carry vapor of the 1,3-bis(diisopropylamino)trisilane into the LPCVD reactor, wherein the LPCVD reactor contains a plurality of vertically oriented and spaced apart silicon wafers (second substrates) heated to 500° C. such that a seed layer of silicon grains is formed on the wafers. Disconnect the 1,3-bis(diisopropylamino)trisilane bubbler. Purge the LPCVD reactor with He gas to remove residual 1,3-bis(diisopropylamino)trisilane therefrom. Then flow He carrier gas through the bubbler to carry vapor of disilane into the LPCVD reactor such that a conformal elemental silicon film is formed on the seed layer of silicon grains disposed on the wafers.

EX. 11 (PROPHETIC)

Replicate Ex. 1 except replace octachlorotrisilane ($Si_3Cl_8$; 11.1 g, 30.1 mmol) with octabromotrisilane ($Si_3Br_8$; 21.8 g, 30.1 mmol) to give a remainder containing 1,3-bis(diisopropylamino)hexabromotrisilane (i-$Pr_2NSiBr_2SiBr_2SiBr_2N$(i-$Pr)_2$).

EX. 12 (PROPHETIC)

Replicate Ex. 2 except replace the remainder of Ex. 1 (containing 1,3-bis(diisopropylamino)hexachlorotrisilane) with the remainder of Ex. 11 (containing 1,3-bis(diisopropylamino)hexabromotrisilane) to give 1,3-bis(diisopropylamino)trisilane (i-$Pr_2NSiH_2SiH_2SiH_2N$(i-$Pr)_2$).

COMPARATIVE EX. 1

<0.01 g of $B(C_6F_5)_3$, 0.02 g of diisopropylamino-disilane (DPDS), 0.03 g of diisopropylamino (DiPAH), and 0.77 g of $d_6$-benzene were combined in a flask and stirred for 1 hour at ambient temperature. By NMR, one could observe a 2% conversion to bis-diisopropylamino-disilane (BisDPDS) with the remaining DPDS unreacted.

COMPARATIVE EX. 2

<0.01 g of $B(C_6F_5)_3$, 0.49 g of DPDS, 1.10 g of DiPAH, and 0.80 g mesitylene were combined in a flask and stirred for 1 hour at ambient temperature. A small amount of bubbling was observed. By NMR, one could observe a 10% conversion to BisDPDS.

EX. 13

0.10 g of 2,2-disilyltrisilane was added to 0.2 g acetonitrile which appeared to form a milky suspension. <0.01 g of $B(C_6F_5)_3$ was added to the mixture and stirred. 0.06 g of DiPAH was added dropwise which resulted in the solution turning yellow and some evolution of gas. The reaction was stirred for 1 h to give around a 10% yield of 1-(diisopropylamino)-2,2-disilyltrisilane as well as a 3% yield of 1,3-bis(diisoproplyamino)-2,2-disilyltrisilane as determined by $^1H$ NMR.

EX. 14 (PROPHETIC)

0.10 g of 2,2,4,4-tetrasilylpentasilane was added to 0.2 g acetonitrile which appeared to form a milky suspension. <0.01 g of $B(C_6F_5)_3$ was added to the mixture and stirred. 0.12 g of DiPAH was added dropwise which resulted in the solution turning yellow and some evolution of gas. The reaction was stirred for 1 h to give 1,5-bis(diisopropylamino)-2,2,4,4-tetrasilylpentasilane and 1,3-bis(diisopropylamine)-2,2,4,4-tetrasilylpentasilane.

The below claims are incorporated by reference here, and the terms "claim" and "claims" are replaced by the term "aspect" or "aspects," respectively. Embodiments of the invention also include these resulting numbered aspects.

Some inventive embodiments are the following numbered aspects:

Aspect 1. A compound of formula (I): ($R^1R^2N)Si_nH_{2n}(NR^3R^4)$ (I), wherein subscript n is an integer from 3 to 9; $R^1$ is methyl, propyl, butyl, pentyl, hexyl, ($C_3$-$C_6$)cycloalkyl, ($C_2$-$C_6$)alkenyl, ($C_2$-$C_6$)alkynyl, or phenyl, and each $R^2$, $R^3$ and $R^4$ independently is ($C_1$-$C_6$)alkyl, ($C_3$-$C_6$)cycloalkyl, ($C_2$-$C_6$)alkenyl, ($C_2$-$C_6$)alkynyl, or phenyl; or $R^1$ is H and each of $R^2$, $R^3$, and $R^4$ independently is ($C_1$-$C_6$)alkyl, ($C_3$-$C_6$)cycloalkyl, ($C_2$-$C_6$)alkenyl, ($C_2$-$C_6$)alkynyl, or phenyl; or $R^1$ and $R^3$ are H and each of $R^2$ and $R^4$ independently is ($C_1$-$C_6$)alkyl, ($C_3$-$C_6$)cycloalkyl, ($C_2$-$C_6$)alkenyl, ($C_2$-$C_6$)alkynyl, or phenyl; or $R^1$ and $R^2$ are bonded together to be —$R^{1a}$—$R^{2a}$— wherein —$R^{1a}$—$R^{2a}$— is ($C_2$-$C_5$)alkylene and each $R^3$ and $R^4$ independently is ($C_1$-$C_6$)alkyl, ($C_3$-$C_6$)cycloalkyl, ($C_2$-$C_6$)alkenyl, ($C_2$-$C_6$)alkynyl, or phenyl; or $R^1$ and $R^2$ are bonded together to be —$R^{1a}$—$R^{2a}$— wherein —$R^{1a}$—$R^{2a}$— is ($C_2$-$C_5$)alkylene and $R^3$ and $R^4$ are bonded together to be —$R^{3a}$—$R^{4a}$— wherein —$R^{3a}$—$R^{4a}$— is ($C_2$-$C_5$)alkylene; or $R^1$ and $R^3$ are bonded together to be —$R^{1a}$—$R^{3a}$— wherein —$R^{1a}$—$R^{3a}$— is ($C_2$-$C_5$)alkylene and each of $R^2$ and $R^4$ independently is ($C_1$-$C_6$)alkyl, ($C_3$-$C_6$)cycloalkyl, ($C_2$-$C_6$)alkenyl, ($C_2$-$C_6$)alkynyl, or phenyl; and the $R^1R^2N$— and —$NR^3R^4$ groups are bonded to a same silicon atom or to different silicon atoms in the compound of formula (I).

Aspect 2. The compound of aspect 1 wherein n is 3.
Aspect 3. The compound of aspect 1 wherein n is 4.
Aspect 4. The compound of aspect 1 wherein n is 5, 6, 7, 8, or 9.
Aspect 5. The compound of any one of aspects 1-4 wherein $R^1$ is methyl, propyl, butyl, pentyl, hexyl, ($C_3$-$C_6$)cycloalkyl, ($C_2$-$C_6$)alkenyl, ($C_2$-$C_6$)alkynyl, or phenyl, and each $R^2$, $R^3$ and $R^4$ independently is ($C_1$-$C_6$)alkyl, ($C_3$-$C_6$)cycloalkyl, ($C_2$-$C_6$)alkenyl, ($C_2$-$C_6$)alkynyl, or phenyl.
Aspect 6. The compound of any one of aspects 1-4 wherein each $R^1$, $R^2$, $R^3$ and $R^4$ independently is methyl, propyl, butyl, pentyl, or hexyl.
Aspect 7. The compound of any one of aspects 1-4 wherein $R^1$ is methyl, propyl, butyl, pentyl, or hexyl and each $R^2$, $R^3$ and $R^4$ independently is ($C_3$-$C_5$)alkyl.
Aspect 8. The compound of any one of aspects 1-4 wherein each $R^1$ and $R^3$ is methyl and each $R^2$ and $R^4$ is isopropyl, sec-butyl, iso-butyl, or tert-butyl; or wherein each $R^1$, $R^2$, $R^3$ and $R^4$ independently is isopropyl, sec-butyl, iso-butyl, or tert-butyl.

Aspect 9. The compound of any one of aspects 1-4 wherein each $R^1$ and $R^3$ is methyl and each $R^2$ and $R^4$ is tert-butyl.

Aspect 10. The compound of any one of aspects 1-4 wherein each $R^1$, $R^2$, $R^3$ and $R^4$ independently is $(C_3-C_4)$ alkyl.

Aspect 11. The compound of any one of aspects 1-4 wherein each $R^1$, $R^2$, $R^3$ and $R^4$ independently is isopropyl.

Aspect 12. The compound of any one of aspects 1-4 wherein each $R^1$, $R^2$, $R^3$ and $R^4$ independently is sec-butyl.

Aspect 13. The compound of any one of aspects 1-4 wherein $R^1$ is $(C_3-C_6)$cycloalkyl.

Aspect 14. The compound of any one of aspects 1-4 wherein $R^1$ is $(C_2-C_6)$alkenyl or $(C_2-C_6)$alkynyl.

Aspect 15. The compound of any one of aspects 1-4 wherein $R^1$ is H.

Aspect 16. The compound of any one of aspects 1-4 wherein $R^1$ is phenyl.

Aspect 17. The compound of any one of aspects 13-16 wherein each $R^2$, $R^3$ and $R^4$ independently is $(C_1-C_6)$alkyl or wherein each $R^3$ is the same as $R^1$ and each $R^4$ is the same as $R^2$.

Aspect 18. The compound of any one of aspects 1-4 wherein $R^1$ and $R^2$ are bonded together to be —$R^{1a}$—$R^{2a}$— wherein —$R^{1a}$—$R^{2a}$— is $(C_3-C_5)$alkylene; and each $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl.

Aspect 19. The compound of any one of aspects 1-4 wherein $R^1$ and $R^2$ are bonded together to be —$R^{1a}$—$R^{2a}$— wherein —$R^{1a}$—$R^{2a}$— is $(C_4$ or $C_5)$alkylene; and each $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl.

Aspect 20. The compound of any one of aspects 1-4 wherein $R^1$ and $R^2$ are bonded together to be —$R^{1a}$—$R^{2a}$— wherein —$R^{1a}$—$R^{2a}$— is $(C_2-C_5)$alkylene and $R^3$ and $R^4$ are bonded together to be —$R^{3a}$—$R^{4a}$— wherein —$R^{3a}$—$R^{4a}$— is $(C_2-C_5)$alkylene.

Aspect 21. The compound of any one of aspects 1-4 wherein $R^1$ and $R^3$ are bonded together to be —$R^{1a}$—$R^{3a}$— wherein —$R^{1a}$—$R^{3a}$— is $(C_2-C_5)$alkylene and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl.

Aspect 22. The compound of any one of aspects 1 to 21 wherein the $R^1R^2N$— and —$NR^3R^4$ groups are bonded to different silicon atoms in the compound of formula (I).

Aspect 23. The compound of aspect 22 comprising a compound of formula (I-a) $R^1R^2N$—$SiH_2SiH_2SiH_2NR^3R^4$ (I-a), wherein $R^1$, $R^2$, $R^3$ and $R^4$ are as defined above.

Aspect 24. The compound of aspect 22 comprising a compound of formula (I-b) $R^1R^2N$—$SiH(SiH_3)SiH_2NR^3R^4$ (I-b), wherein $R^1$, $R^2$, $R^3$ and $R^4$ are as defined above.

Aspect 25. The compound of any one of the preceding aspects comprising a compound of formula (I-c) $R^1R^2N$—$SiH_2SiH_2SiH_2SiH_2NR^3R^4$ (I-c), wherein $R^1$ $R^2$, $R^3$ and $R^4$ are as defined above.

Aspect 26. The compound of aspect 22 comprising a compound of formula (I-d) $R^1R^2N$—$SiH(SiH_3)SiH_2SiH_2NR^3R^4$ (I-d), wherein $R^1$, $R^2$, $R^3$ and $R^4$ are as defined above.

Aspect 27. The compound of aspect 22 comprising a compound of formula (I-e) $R^1R^2N$—$SiH_2SiH(SiH_3)SiH_2NR^3R^4$ (I-e), wherein $R^1$, $R^2$, $R^3$ and $R^4$ are as defined above.

Aspect 28. The compound of aspect 22 comprising a compound of formula (I-f) $R^1R^2N$—$Si(SiH_3)_2SiH_2NR^3R^4$ (I-f), wherein $R^1$, $R^2$, $R^3$ and $R^4$ are as defined above.

Aspect 29. The compound of aspect 22 comprising a compound of formula (I-g) $R^1R^2N$—$SiH_2SiH_2SiH_2SiH_2SiH_2NR^3R^4$ (I-g), wherein $R^1$, $R^2$, $R^3$ and $R^4$ are as defined above.

Aspect 30. The compound of aspect 22 comprising a compound of formula (I-h) $R^1R^2N$—$SiH(SiH_3)SiH_2SiH_2SiH_2NR^3R^4$ (I-h), wherein $R^1$, $R^2$, $R^3$ and $R^4$ are as defined above.

Aspect 31. The compound of aspect 22 comprising a compound of formula (I-i) $R^1R^2N$—$SiH_2SiH(SiH_3)SiH_2SiH_2NR^3R^4$ (I-i), wherein $R^1$, $R^2$, $R^3$ and $R^4$ are as defined above.

Aspect 32. The compound of aspect 22 comprising a compound of formula (I-j) $R^1R^2N$—$SiH_2SiH_2SiH(SiH_3)SiH_2NR^3R^4$ (I-j), wherein $R^1$, $R^2$, $R^3$ and $R^4$ are as defined above.

Aspect 33. The compound of aspect 22 comprising a compound of formula (I-k) $R^1R^2N$—$SiH(SiH_2SiH_3)SiH_2SiH_2NR^3R^4$ (I-k), wherein $R^1$, $R^2$, $R^3$ and $R^4$ are as defined above.

Aspect 34. The compound of aspect 22 comprising a compound of formula (I-l) $R^1R^2N$—$SiH_2Si(SiH_3)_2SiH_2NR^3R^4$ (I-l), wherein $R^1$, $R^2$, $R^3$ and $R^4$ are as defined above.

Aspect 35. The compound of aspect 22 wherein the $R^1R^2N$— and —$NR^3R^4$ groups are bonded to different terminal silicon atoms of a compound of formula (I-m): $R^1R^2N$—$(SiH_2)_n$—$NR^3R^4$ (I-m), wherein n, $R^1$, $R^2$, $R^3$ and $R^4$ are as defined above.

Aspect 36. The compound of aspect 22 comprising a compound of formula (I-n) $R^1R^2N$—$SiH_2Si(SiH_3)_2SiH_2Si(SiH_3)_2SiH_2NR^3R^4$ (I-n), wherein $R^1$, $R^2$, $R^3$ and $R^4$ are as defined above.

Aspect 37. The compound of aspect 26 comprising a compound of formula (I-o) $R^1R^2N$—$SiH_2Si(SiH_3)_2SiH(NR^3R^4)Si(SiH_3)_3$ (I-o), wherein $R^1$, $R^2$, $R^3$ and $R^4$ are as defined above.

Aspect 38. The compound of any one of aspects 1 to 21 wherein the $R^1R^2N$— and —$NR^3R^4$ groups are bonded to a same silicon atom in the compound of formula (I)

Aspect 39. The compound of aspect 38 comprising a compound of formula (I-aa) $R^1R^2N$—$SiH(NR^3R^4)SiH_2SiH_3$ (I-aa), wherein $R^1$, $R^2$, $R^3$ and $R^4$ are as defined above.

Aspect 40. The compound of aspect 38 comprising a compound of formula (I-bb) $R^1R^2N$—$Si(NR^3R^4)(SiH_3)SiH_3$ (I-bb), wherein $R^1$, $R^2$, $R^3$ and $R^4$ are as defined above.

Aspect 41. The compound of aspect 38 comprising a compound of formula (I-cc) $R^1R^2N$—$SiH(NR^3R^4)SiH_2SiH_2SiH_3$ (I-cc), wherein $R^1$ $R^2$, $R^3$ and $R^4$ are as defined above.

Aspect 42. The compound of aspect 38 comprising a compound of formula (I-dd) $R^1R^2N$—$Si(NR^3R^4)(SiH_3)SiH_2SiH_3$ (I-dd), wherein $R^1$, $R^2$, $R^3$ and $R^4$ are as defined above.

Aspect 43. The compound of aspect 38 comprising a compound of formula (I-ee) $R^1R^2N$—$SiH(NR^3R^4)SiH(SiH_3)SiH_3$ (I-ee), wherein $R^1$, $R^2$, $R^3$ and $R^4$ are as defined above.

Aspect 44. The compound of aspect 38 comprising a compound of formula (I-ff) $R^1R^2N$—$SiH(NR^3R^4)SiH_2SiH_2SiH_2SiH_3$ (I-ff), wherein $R^1$, $R^2$, $R^3$ and $R^4$ are as defined above.

Aspect 45. The compound of aspect 38 comprising a compound of formula (I-gg) $R^1R^2N$—$Si(NR^3R^4)(SiH_3)SiH_2SiH_2SiH_3$ (I-gg), wherein $R^1$, $R^2$, $R^3$ and $R^4$ are as defined above.

Aspect 46. The compound of aspect 38 comprising a compound of formula (I-hh) $R^1R^2N$—$SiH(NR^3R^4)SiH(SiH_3)SiH_2SiH_3$ (I-hh), wherein $R^1$, $R^2$, $R^3$ and $R^4$ are as defined above.

Aspect 47. The compound of aspect 38 comprising a compound of formula (I-ii) $R^1R^2N$—$SiH(NR^3R^4)SiH_2SiH(SiH_3)SiH_3$ (I-ii), wherein $R^1$, $R^2$, $R^3$ and $R^4$ are as defined above.

Aspect 48. The compound of aspect 38 comprising a compound of formula (I-jj) $R^1R^2N$—$Si(NR^3R^4)(SiH_2SiH_3)SiH_2SiH_3$ (I-jj), wherein $R^1$, $R^2$, $R^3$ and $R^4$ are as defined above.

Aspect 49. The compound of aspect 38 comprising a compound of formula (I-kk) $R^1R^2N$—$SiH(NR^3R^4)Si(SiH_3)_2SiH_3$ (I-kk), wherein $R^1$, $R^2$, $R^3$ and $R^4$ are as defined above.

Aspect 50. The compound of aspect 38 comprising a compound of formula (I-ll) $R^1R^2N$—$SiH(NR^3R^4)Si(SiH_3)_2SiH_2Si(SiH_3)_3$ (I-ll), wherein $R^1$, $R^2$, $R^3$ and $R^4$ are as defined above.

Aspect 51. A compound that is 1,1-bis(diisopropylamino)trisilane; 1,2-bis(diisopropylamino)trisilane; 1,3-Bis(diisopropylamino)trisilane; 2,2-bis(diisopropylamino)trisilane; 1,2-bis(diisopropylamino)tetrasilane; 1,3-bis(diisopropylamino)tetrasilane; 1,4-bis(diisopropylamino)tetrasilane; 1,5-bis(diisopropylamino)pentasilane; 1,3-bis(diisopropylamino)-2,2-disilyltrisilane; 1,1-bis(diisopropylamino)-2,2-disilyltrisilane; or 1,5-bis(diisopropylamine),2,2,4,4-tetrasilylpentasilane.

Aspect 52. A composition comprising the compound of any one of the preceding aspects and at least one additional ingredient that is different than the compound of any one of the preceding aspects.

Aspect 53. The composition of aspect 52, wherein the at least one silane is a silane compound having from 1 to 5 silicon atoms, hydrogen and/or halogen atoms, and lacking a nitrogen atom.

Aspect 54. The composition of aspect 52 comprising 1,3-bis(diisopropylamino)trisilane and at least one of 1-(diisopropylamino)trisilane, (diisopropylamino)disilane, and (diisopropylamino)silane.

Aspect 55. A method of making a compound of formula (I): $(R^1R^2N)Si_nH_{2n}(NR^3R^4)$ (I), wherein subscript n is an integer from 3 to 9; $R^1$ is methyl, propyl, butyl, pentyl, hexyl, $(C_3-C_6)$cycloalkyl, $(C_2-C_6)$alkenyl, $(C_2-C_6)$alkynyl, or phenyl, and each $R^2$, $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ is H and each of $R^2$, $R^3$, and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^3$ are H and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be —$R^{1a}$—$R^{2a}$— wherein —$R^{1a}$—$R^{2a}$— is $(C_2-C_5)$alkylene and each $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be —$R^{1a}$—$R^{2a}$— wherein —$R^{1a}$—$R^{2a}$— is $(C_2-C_5)$alkylene and $R^3$ and $R^4$ are bonded together to be —$R^{3a}$—$R^{4a}$— wherein —$R^{3a}$—$R^{4a}$— is $(C_2-C_5)$alkylene; or $R^1$ and $R^3$ are bonded together to be —$R^{1a}$—$R^{3a}$— wherein —$R^{1a}$—$R^{3a}$— is $(C_2-C_5)$alkylene and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; and the $R^1R^2N$— and —$NR^3R^4$ groups are bonded to a same silicon atom or to different silicon atom in the compound of formula (I), the method comprising: Contacting a compound of formula (c1): $(R^1R^2N)Si_nX_{2n}(NR^3R^4)$ (c1), wherein each X independently is a halogen atom selected from Cl, Br, and I; and n, $R^1$, $R^2$, $R^3$, and $R^4$ are as defined above; and the $R^1R^2N$— and $R^3R^4N$— groups are bonded to a same silicon atom or to different silicon atoms in the compound of formula (c1), with an aluminum hydride to give a mixture of the compound of formula (I) and at least one reaction by-product.

Aspect 56. The method of aspect 55 wherein each X is Cl and the aluminum hydride is $LiAlH_4$.

Aspect 57. The method of aspect 54 or 56 wherein the contacting step further comprises an alkylene glycol dialkyl ether vehicle, wherein the compound of formula (c1) and the aluminum hydride are in admixture with the alkylene glycol dialkyl ether vehicle during the contacting step.

Aspect 58. The method of aspect 55, 56, or 57, further comprising a preliminary step of contacting one molar equivalent of a compound of formula (a1): $R^1R^2NM$ (a1) and one molar equivalent of a compound of formula (a2): $R^3R^4NM$ (a2), or contacting one molar equivalent of a compound of formula (a3) $M(R^2)N$—$R^{1a}$—$R^{3a}$—$N(R^4)M$ (a3), with a compound of formula (b1): $Si_nX_{2n+2}$ (b1) to give the compound of formula (c1), wherein each M independently is a Group I element selected from H, Li, Na, and K; and X, n, $R^1$, $R^2$, $R^3$, and $R^4$ are as defined above.

Aspect 59. The method of aspect 58 wherein M is Li.

Aspect 60. The method of aspect 58 or 59 wherein the contacting step further comprises a hydrocarbon vehicle, wherein the compounds of formulas (a1), (a2), and (b1) or the compounds of formulas (a3) and (b1) are in admixture with the hydrocarbon vehicle during the contacting step.

Aspect 61. The method of any one of aspects 55 to 58 further comprising a subsequent step of separating the compound of formula (I) from the reaction by-product(s) to give a purified compound of formula (I).

Aspect 62. A method of making a silicon-containing material, the method comprising subjecting a source gas comprising the compound of any one of aspects 1-48 to chemical vapor deposition conditions or atomic layer deposition conditions in the presence of a substrate, to give a silicon-containing material formed on the substrate.

Aspect 63. The method of aspect 62, wherein the silicon-containing material comprises elemental silicon, silicon carbide, silicon nitride, silicon oxide, silicon oxynitride, or silicon-carbo-nitride.

Aspect 64. A compound of formula (c1): $(R^1R^2N)Si_nX_{2n}(NR^3R^4)$ (c1), wherein subscript n is an integer from 3 to 9; $R^1$ is methyl, propyl, butyl, pentyl, hexyl, $(C_3-C_6)$cycloalkyl, $(C_2-C_6)$alkenyl, $(C_2-C_6)$alkynyl, or phenyl, each $R^2$, $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ is H and each of $R^2$, $R^3$, and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^3$ are H and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be —$R^{1a}$—$R^{2a}$— wherein —$R^{1a}$—$R^{2a}$— is $(C_2-C_5)$alkylene and each $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be —$R^{1a}$—$R^{2a}$— wherein —$R^{1a}$—$R^{2a}$— is $(C_2-C_5)$alkylene and $R^3$ and $R^4$ are bonded together to be —$R^{3a}$—$R^{4a}$— wherein —$R^{3a}$—$R^{4a}$— is $(C_2-C_5)$alkylene; or $R^1$ and $R^3$ are bonded together to be —$R^{1a}$—$R^{3a}$— wherein —$R^{1a}$—$R^{3a}$— is $(C_2-C_5)$alkylene and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; and the $R^1R^2N$— and —$NR^3R^4$ groups are bonded to a same silicon atom or to different silicon atoms in the compound of formula (c1).

Aspect 65. A compound of formula (c1): $(R^1R^2N)Si_nX_{2n}(NR^3R^4)$ (c1), wherein X is Cl and n, $R^1$, $R^2$, $R^3$ and $R^4$ are as defined in any one of aspects 2 to 21.

Aspect 66. A compound that is 1,1-Bis(diisopropylamino)hexachlorotrisilane; 1,2-bis(diisopropylamino)hexachlorotrisilane; 1,3-Bis(diisopropylamino)hexachlorotrisilane; 2,2-bis(diisopropylamino)hexachlorotrisilane; 1,2-bis(diisopropylamino)octachlorotetrasilane; 1,3-is(diisopropylamino)octachlorotetrasilane; 1,4-bis(diisopropylamino)octachlorotetrasilane; 1,5-bis(diisopropylamino)decachloropentasilane; 1,3-bis(diisopropylamino)-decachloro-2,2-bissilyltrisilane; 1,1-bis(diisopropylamino)-decachloro-2,2-bissilyltrisilane; 1,1-bis(diisopropylamino)hexabromotrisilane; 1,2-bis(diisopropylamino)hexabromotrisilane; 1,3-Bis(diisopropylamino)hexabromotrisilane; 2,2-bis(diisopropylamino)hexabromotrisilane; 1,2-bis(diisopropylamino)octabromotetrasilane; 1,3-bis(diisopropylamino)octabromotetrasilane; 1,4-bis(diisopropylamino)octabromotetrasilane; 1,5-bis(diisopropylamino)decabromopentasilane; 1,3-bis(diisopropylamino)-decabromo-2,2-bissilyltrisilane; or 1,1-bis(diisopropylamino)-decabromo-2,2-bissilyltrisilane.

Aspect 67. A method of making a compound of formula (c1): $(R^1R^2N)Si_nX_{2n}(NR^3R^4)$ (c1), wherein subscript n is an integer from 3 to 9; each X independently is a halogen atom selected from Cl, Br, and I; $R^1$ is methyl, propyl, butyl, pentyl, hexyl, $(C_3-C_6)$cycloalkyl, $(C_2-C_6)$alkenyl, $(C_2-C_6)$alkynyl, or phenyl, each $R^2$, $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ is H and each of $R^2$, $R^3$, and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^3$ are H and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be $-R^{1a}-R^{2a}-$ wherein $-R^{1a}-R^{2a}-$ is $(C_2-C_5)$alkylene and each $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be $-R^{1a}-R^{2a}-$ wherein $-R^{1a}-R^{2a}-$ is $(C_2-C_5)$alkylene and $R^3$ and $R^4$ are bonded together to be $-R^{3a}-R^{4a}-$ wherein $-R^{3a}-R^{4a}-$ is $(C_2-C_5)$alkylene; or $R^1$ and $R^3$ are bonded together to be $-R^{1a}-R^{3a}-$ wherein $-R^{1a}-R^{3a}-$ is $(C_2-C_5)$alkylene and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; and the $R^1R^2N-$ and $-NR^3R^4$ groups are bonded to a same silicon atom or to different silicon atoms in the compound of formula (c1), the method comprising: Contacting one molar equivalent of a compound of formula (a1): $R^1R^2NM$ (a1) and one molar equivalent of a compound of formula (a2): $R^3R^4NM$ (a2) with a compound of formula (b1): $Si_nX_{2n+2}$ (b1), or contacting one molar equivalent of a compound of formula (a3) $M(R^2)N-R^{1a}-R^{3a}-N(R^4)M$ (a3) with a compound of formula (b1), to give a compound of formula (c1): $(R^1R^2N)Si_nX_{2n}(NR^3R^4)$ (c1), wherein each M independently is a Group I element selected from H, Li, Na, and K; each X independently is a halogen atom selected from Cl, Br, and I; and n, $R^1$, $R^2$, $R^3$, and $R^4$ are as defined immediately above; and the $R^1R^2N-$ and $-NR^3R^4$ groups are bonded to a same silicon atom or to different silicon atoms in the compound of formula (c1).

Aspect 68. The method of aspect 67 wherein X is Cl and n, $R^1$, and $R^2$ are as described in any one of aspects 2 to 21.

Aspect 69. A method of making a silicon-containing material, the method comprising subjecting a source gas comprising a compound of formula (II): $(Et_2N)Si_nH_{2n}(NEt_2)$ (II), wherein subscript n is an integer from 3 to 9, Et is ethyl, and the $Et_2N-$ and $-NEt_2$ groups are bonded to a same silicon atom or to different silicon atoms in the compound of formula (II), to chemical vapor deposition conditions or atomic layer deposition conditions in the presence of a substrate, to give a silicon-containing material formed on the substrate.

Aspect 70. The method of aspect 69 wherein the $Et_2N-$ and $-NEt_2$ groups are bonded to different silicon atoms in the compound of formula (II).

Aspect 71. The method of aspect 69 wherein the $Et_2N-$ and $-NEt_2$ groups are bonded to a same silicon atom in the compound of formula (II).

Aspect 72. Use of the compound of any one of aspects 1-51 in the making of a silicon-containing material comprising elemental silicon, silicon carbide, silicon nitride, silicon oxide, silicon oxynitride, or silicon-carbo-nitride.

Aspect 73. Use of a compound of formula (c1): $(R^1R^2N)Si_nX_{2n}(NR^3R^4)$ (c1) in the synthesis of the compound of formula (I) of any one of aspects 1-48, wherein subscript n is an integer from 3 to 9; each X independently is a halogen atom selected from Cl, Br, and I; and $R^1$ independently is methyl, propyl, butyl, pentyl, hexyl, $(C_3-C_6)$cycloalkyl, $(C_2-C_6)$alkenyl, $(C_2-C_6)$alkynyl, or phenyl, each $R^2$, $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ is H and each of $R^2$, $R^3$, and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^3$ are H and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be $-R^{1a}-R^{2a}-$ wherein $-R^{1a}-R^{2a}-$ is $(C_2-C_5)$alkylene and each $R^3$ and $R^4$ independently is $(C_1-C_6)$alkyl, $(C_3-C_6)$cycloalkyl, $(C_2-C_6)$alkenyl, $(C_2-C_6)$alkynyl, or phenyl; or $R^1$ and $R^2$ are bonded together to be $-R^{1a}-R^{2a}-$ wherein $-R^{1a}-R^{2a}-$ is $(C_2-C_5)$alkylene and $R^3$ and $R^4$ are bonded together to be $-R^{3a}-R^{4a}-$ wherein $-R^{3a}-R^{4a}-$ is $(C_2-C_5)$alkylene; or $R^1$ and $R^3$ are bonded together to be $-R^{1a}-R^{3a}-$ wherein $-R^{1a}-R^{3a}-$ is $(C_2-C_5)$alkylene and each of $R^2$ and $R^4$ independently is $(C_1-C_6)$alkyl, $(C_3-C_6)$cycloalkyl, $(C_2-C_6)$alkenyl, $(C_2-C_6)$alkynyl, or phenyl; and the $R^1R^2N-$ and $-NR^3R^4$ groups are bonded to a same silicon atom or to different silicon atoms in the compound of formula (c1).

Aspect 74. A method of making a compound of formula (I), the method comprising: contacting a compound of formula (d1): $(R^1R^2N)Si_nH_{2n+1}$ (d1) with a compound of formula (d2) $HNR^3R^4$ (d2), wherein n, $R^1$, $R^2$, $R^3$, and $R^4$ are as defined above, in the presence of a main group element catalyst, to give a reaction mixture of the compound of formula (I).

What is claimed is:
1. A compound of formula

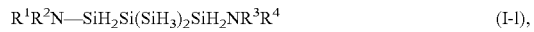

$R^1R^2N-SiH_2Si(SiH_3)_2SiH_2NR^3R^4$     (I-l),

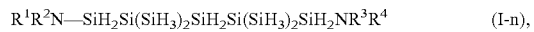

$R^1R^2N-SiH_2Si(SiH_3)_2SiH_2Si(SiH_3)_2SiH_2NR^3R^4$     (I-n),

$R^1R^2N-SiH(NR^3R^4)SiH(SiH_3)SiH_2SiH_3$     (I-hh), or

$R^1R^2N-SiH(NR^3R^4)Si(SiH_3)_2SiH_2Si(SiH_3)_3$     (I-ll), wherein $R^1$ is methyl, propyl, butyl, pentyl, hexyl, or $(C_3-C_6)$cycloalkyl, and each $R^2$, $R^3$ and $R^4$ independently is $(C_1-C_6)$alkyl or $(C_3-C_6)$cycloalkyl; or $R^1$ and $R^2$ are bonded together to be $-R^{1a}-R^{2a}-$ wherein $-R^{1a}-R^{2a}-$ is $(C_2-C_5)$alkylene and each $R^3$ and $R^4$ independently is $(C_1-C_6)$alkyl or $(C_3-C_6)$cycloalkyl; or $R^1$ and $R^2$ are bonded together to be $-R^{1a}-R^{2a}-$ wherein $-R^{1a}-R^{2a}-$ is $(C_2-C_5)$alkylene and $R^3$ and $R^4$ are bonded together to be $-R^{3a}-R^{4a}-$ wherein $-R^{3a}-R^{4a}-$ is $(C_2-C_5)$alkylene; or $R^1$ and $R^3$ are bonded together to be $-R^{1a}-R^{3a}-$ wherein $-R^{1a}-R^{3a}-$ is $(C_2-C_5)$alkylene and each of $R^2$ and $R^4$ independently is $(C_1-C_6)$alkyl or $(C_3-C_6)$cycloalkyl.

2. A compound of claim 1 that is 1,3-bis(diisopropylamino)-2,2-disilyltrisilane; 1,1-bis(diisopropylamino)-2,2-disilyltrisilane, 1,5-bis(diisopropylamino)-2,2,4,4-tetrasilylpentasilane; or 1,1-bis(diisopropylamino)-2,2,4,4-tetrasilylpentasilane.

3. A composition comprising the compound of claim 1 and at least one additional ingredient that is different than the compound of any one of the preceding claims.

4. A method of making the compound of claim 1 of formula $$R^1R^2N-SiH_2Si(SiH_3)_2SiH_2NR^3R^4 \quad (I\text{-}l),$$

$$R^1R^2N-SiH_2Si(SiH_3)_2SiH_2Si(SiH_3)_2SiH_2NR^3R^4 \quad (I\text{-}n),$$

$$R^1R^2N-SiH(NR^3R^4)SiH(SiH_3)SiH_2SiH_3 \quad (I\text{-}hh),$$

or $$R^1R^2N-SiH(NR^3R^4)Si(SiH_3)_2SiH_2Si(SiH_3)_3 \quad (I\text{-}II),$$

$R^1$ is methyl, propyl, butyl, pentyl, hexyl, or $(C_3-C_6)$cycloalkyl, and each $R^2$, $R^3$ and $R^4$ independently is $(C_1-C_6)$alkyl or $(C_3-C_6)$cycloalkyl; or $R^1$ and $R^2$ are bonded together to be $-R^{1a}-R^{2a}-$ wherein $-R^{1a}-R^{2a}-$ is $(C_2-C_5)$alkylene and each $R^3$ and $R^4$ independently is $(C_1-C_6)$alkyl or $(C_3-C_6)$cycloalkyl; or $R^1$ and $R^2$ are bonded together to be $-R^{1a}-R^{2a}-$ wherein $-R^{1a}-R^{2a}-$ is $(C_2-C_5)$alkylene and $R^3$ and $R^4$ are bonded together to be $-R^{3a}-R^{4a}-$ wherein $-R^{3a}-R^{4a}-$ is $(C_2-C_5)$alkylene; or $R^1$ and $R^3$ are bonded together to be $-R^{1a}-R^{3a}-$ wherein $-R^{1a}-R^{3a}-$ is $(C_2-C_6)$alkylene and each of $R^2$ and $R^4$ independently is $(C_1-C_6)$alkyl or $(C_3-C_6)$cycloalkyl, the method comprising:

Contacting a compound of formula (c1):

$$(R^1R^2N)Si_nX_{2n}(NR^3R^4) \quad (c1),$$

wherein each X independently is a halogen atom selected from Cl, Br, and I; n is 5 or 9, and $R^1$, $R^2$, $R^3$, and $R^4$ are as defined above, and where the compound of formula (c1) has the same silicon backbone structure as in one of formulas (I-l), (I-n), (I-hh), or (I-II), with an aluminum hydride to give a mixture of the compound of formula (I-l), (I-n), (I-hh), or (I-II) and at least one reaction by-product.

5. A method of making a silicon-containing material, the method comprising subjecting a source gas comprising the compound of claim 1 to chemical vapor deposition conditions or atomic layer deposition conditions in the presence of a substrate, to give a silicon-containing material formed on the substrate.

6. A method of making a compound as in claim 1 of formula $$R^1R^2N-SiH_2Si(SiH_3)_2SiH_2NR^3R^4 \quad (I\text{-}l),$$

$$R^1R^2N-SiH_2Si(SiH_3)_2SiH_2Si(SiH_3)_2SiH_2NR^3R^4 \quad (I\text{-}n),$$

$$R^1R^2N-SiH(NR^3R^4)SiH(SiH_3)SiH_2SiH_3 \quad (I\text{-}hh),$$

or $$R^1R^2N-SiH(NR^3R^4)Si(SiH_3)_2SiH_2Si(SiH_3)_3 \quad (I\text{-}II)$$

$R^1$ is methyl, propyl, butyl, pentyl, hexyl, or $(C_3-C_6)$cycloalkyl, and each $R^2$, $R^3$ and $R^4$ independently is $(C_1-C_6)$alkyl or $(C_3-C_6)$cycloalkyl; or $R^1$ and $R^2$ are bonded together to be $-R^{1a}-R^{2a}-$ wherein $-R^{1a}-R^{2a}-$ is $(C_2-C_5)$alkylene and each $R^3$ and $R^4$ independently is $(C_1-C_6)$alkyl or $(C_3-C_6)$cycloalkyl; or $R^1$ and $R^2$ are bonded together to be $-R^{1a}-R^{2a}-$ wherein $-R^{1a}-R^{2a}-$ is $(C_2-C_5)$alkylene and $R^3$ and $R^4$ are bonded together to be $-R^{3a}-R^{4a}-$ wherein $-R^{3a}-R^{4a}-$ is $(C_2-C_5)$alkylene; or $R^1$ and $R^3$ are bonded together to be $-R^{1a}-R^{3a}-$ wherein $-R^{1a}-R^{3a}-$ is $(C_2-C_5)$alkylene and each of $R^2$ and $R^4$ independently is $(C_1-C_6)$alkyl or $(C_3-C_6)$cycloalkyl, the method comprising:

Contacting a compound of formula (d1):

$$(R^1R^2N)Si_nH_{2n+1} \quad (d1)$$

with a compound of formula (d2)

$$(HNR^3R^4) \quad (d2),$$

wherein n is 5 or 9, $R^1$, $R^2$, $R^3$, and $R^4$ are as defined above, and where the compound of formula (d1) has the same silicon backbone structure as in one of formulas (I-l), (I-n), (I-hh), or (I-II), in the presence of a catalyst, wherein the catalyst comprises at least one of the main group elements Li, Na, K, Rb, Cs, Be, Mg, Ca, Sr, Ba, B, Al, Ga, In, Tl, C, Si, Ge, Sn, Pb, N, P, As, Bb, Bi, O, S, Se, Te, F, Cl, Br, I, Zn, Cd, or Hg to give a reaction mixture;

maintaining the reaction mixture ast a temperature between about 0° C. to about 250° C.;

allowing the reaction to proceed to form the compound of formula (I) above; separating the compound of formula (I) of the compound of formula (I) from the reaction mixture;

wherein the reaction mixture temperature may vary during the synthesis and is maintained such that the temperature of the reaction mixture is not allowed to drop below about 0° C. and not exceed about 250° C.

7. The method of claim 6, wherein the catalyst comprises at least one of the elements Mg, Ca, Sr, Ba, B, Al, Ga, Ge or Sn.

* * * * *